United States Patent
Honma et al.

(10) Patent No.: US 12,400,742 B2
(45) Date of Patent: Aug. 26, 2025

(54) PROGRAM, INFORMATION PROCESSING DEVICE, AND INFORMATION PROCESSING METHOD

(71) Applicant: TERUMO KABUSHIKI KAISHA, Tokyo (JP)

(72) Inventors: Yasuyuki Honma, Kanagawa (JP); Naoyuki Maeda, Odawara (JP); Takayuki Uchida, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 125 days.

(21) Appl. No.: 18/178,303

(22) Filed: Mar. 3, 2023

(65) Prior Publication Data
US 2023/0207073 A1 Jun. 29, 2023

Related U.S. Application Data

(63) Continuation of application No. PCT/JP2021/032289, filed on Sep. 2, 2021.

(30) Foreign Application Priority Data

Sep. 8, 2020 (JP) .............................. 2020-150747

(51) Int. Cl.
*G16H 10/20* (2018.01)
*G06F 3/0481* (2022.01)
(Continued)

(52) U.S. Cl.
CPC ........... *G16H 10/20* (2018.01); *G06F 3/0481* (2013.01); *G06F 3/04842* (2013.01);
(Continued)

(58) Field of Classification Search
CPC ... G16H 10/20; G06F 3/0481; G06F 3/04842; G06V 40/165; G06V 40/20; G10L 15/22; G10L 15/26; G10L 25/66
See application file for complete search history.

(56) References Cited

U.S. PATENT DOCUMENTS

| 12,121,360 B2 * | 10/2024 | Huggins | ................. A61F 4/00 |
| 2007/0179363 A1 * | 8/2007 | Stupp | ..................... G16H 50/30 |
| | | | 128/920 |

(Continued)

FOREIGN PATENT DOCUMENTS

| JP | 2017217051 A | 12/2017 |
| JP | 2020000483 A | 1/2020 |

(Continued)

OTHER PUBLICATIONS

T. Mabutchi, T. Takeda, N. Kubota and T. Matuda, "Aphasia Rehabilitation Support System by Using Multimodal Interface Device," 2015 IEEE International Conference on Systems, Man, and Cybernetics, Hong Kong, China, 2015, pp. 1433-1438, doi: 10.1109/SMC.2015.254. (Year: 2015).*

(Continued)

*Primary Examiner* — Sun M Li
(74) *Attorney, Agent, or Firm* — Buchanan Ingersoll & Rooney PC

(57) ABSTRACT

A non-transitory computer-readable medium, an information processing device, and an information processing method that causes a computer processor to execute a process that includes: outputting a first question by voice; receiving an answer to the first question from a subject; outputting a second question by text; receiving an answer to the second question from the subject; determining whether or not the answers to the first and second questions are correct; and estimating a possibility of a brain dysfunction of the subject (Continued)

based on correctness or incorrectness of the answers to the first and second questions.

17 Claims, 16 Drawing Sheets

(51) Int. Cl.
| | |
|---|---|
| *G06F 3/04842* | (2022.01) |
| *G06V 40/16* | (2022.01) |
| *G06V 40/20* | (2022.01) |
| *G10L 15/22* | (2006.01) |
| *G10L 15/26* | (2006.01) |
| *G10L 25/66* | (2013.01) |

(52) U.S. Cl.
CPC ............ *G06V 40/165* (2022.01); *G06V 40/20* (2022.01); *G10L 15/22* (2013.01); *G10L 15/26* (2013.01); *G10L 25/66* (2013.01)

(56) References Cited

U.S. PATENT DOCUMENTS

| | | | | |
|---|---|---|---|---|
| 2008/0287821 | A1* | 11/2008 | Jung | G16H 40/63 600/544 |
| 2016/0314784 | A1* | 10/2016 | Kleppe | G10L 15/19 |
| 2018/0103885 | A1* | 4/2018 | Wrenn | G16H 10/20 |
| 2018/0349560 | A1 | 12/2018 | Mccloskey et al. | |
| 2019/0110728 | A1* | 4/2019 | Sbodio | G09B 7/00 |
| 2019/0311815 | A1* | 10/2019 | Kim | A61B 5/4088 |
| 2022/0293266 | A1* | 9/2022 | Choi | G16H 10/60 |
| 2022/0293286 | A1* | 9/2022 | Kim | A61B 5/7267 |

FOREIGN PATENT DOCUMENTS

| | | | | |
|---|---|---|---|---|
| JP | 6729923 | B1 | 7/2020 | |
| JP | 2020525061 | A | 8/2020 | |
| WO | 2014002349 | A1 | 1/2014 | |
| WO | WO-2020013302 | A1 * | 1/2020 | ........... A61B 5/0022 |
| WO | WO-2021213935 | A1 * | 10/2021 | ........... A61B 5/4082 |
| WO | 2018/219486 | A1 | 1/2024 | |

OTHER PUBLICATIONS

Y. J. Tian, Y. H. Tai, T. H. Kuo and K. T. Sun, "Reactions of Brain in English Reading Tests," 2013 Fourth Global Congress on Intelligent Systems, Hong Kong, China, 2013, pp. 309-313, doi: 10.1109/GCIS.2013.56. (Year: 2013).*

A. Roman-Gonzalez, N. I. Vargas-Cuentas, M. Hoyos, J. Diaz and M. Zimic, "Brain computer interface to answer yes-no questions," 2017 2nd International Conference on Bio-engineering for Smart Technologies (BioSMART), Paris, France, 2017, pp. 1-4, doi: 10.1109/BIOSMART.2017.8095323. (Year: 2017).*

A. Plerou and C. Bobori, "Memory disorders within the frame of algorithmic thinking: Brain imaging evidence," 2015 IEEE International Symposium on Signal Processing and Information Technology (ISSPIT), Abu Dhabi, United Arab Emirates, 2015, pp. 381-386, doi: 10.1109/ISSPIT.2015.7394364. (Year: 2015).*

Auditory-Perceptual Assessment of Fluency in Typical and Neurologically Disordered Speech, by Nelly Penttilä,a Anna-Maija Korpijaakko-Huuhka,a and Ray D. Kentb Journal of Speech, Language, and Hearing Research · vol. 61 · 1086-1103 · May 2018 (Year: 2018).*

Janzen, T. B., & Thaut, M. H. (2018). Rethinking the role of music in the neurodevelopment of autism spectrum disorder. Music & Science, 1. https://doi.org/10.1177/2059204318769639 (Original work published 2018) (Year: 2018).*

D. Le, K. Licata, C. Persad and E. M. Provost, "Automatic Assessment of Speech Intelligibility for Individuals With Aphasia," in IEEE/ACM Transactions on Audio, Speech, and Language Processing, vol. 24, No. 11, pp. 2187-2199, Nov. 2016, doi: 10.1109/TASLP.20162598428. (Year: 2016).*

International Search Report (PCT/ISA/210) with translation and Written Opinion (PCT/ISA/237) mailed on Nov. 22, 2021, by the Patent Office as the International Searching Authority for International Application No. PCT/JP2021/032289. 10 pages.

English Translations of the International Search Report (Form PCT/ISA/210) and the Written Opinion of the International Searching Authority (Form PCT/ISA/237) issued Nov. 22, 2021, by the Japan Patent Office in corresponding International Application No. PCT/JP2021/032289. (5 pages).

Extended European Search Report issued in corresponding European U.S. Appl. No. 21/866,646, dated Jan. 23, 2024.

* cited by examiner

FIG. 9

| DATE AND TIME | SUBJECT | VOICE | TEXT | REACTION ||||| ESTIMATION RESULT | IMAGE |
| --- | --- | --- | --- | --- | --- | --- | --- | --- | --- | --- |
| | | | | SYMMETRY OF FACE | FINGER/ LINE OF SIGHT | EXPRESSION | ... | ANSWERING TIME | | |
| 2019/4/1 | TARO YAMADA | WRONG ANSWER | CORRECT ANSWER | — | ABNORMAL | PERPLEXED | ... | *** | DEMENTIA | *** |
| ... | ... | ... | ... | ... | ... | ... | ... | ... | ... | ... |

PROGRAM, INFORMATION PROCESSING DEVICE, AND INFORMATION PROCESSING METHOD

CROSS-REFERENCES TO RELATED APPLICATIONS

This application is a continuation of International Application No. PCT/JP2021/032289 filed on Sep. 2, 2021, which claims priority to Japanese Application No. 2020-150747 filed on Sep. 8, 2020, the entire content of both of which is incorporated herein by reference.

TECHNOLOGICAL FIELD

The present disclosure generally relates to a program, an information processing device, and an information processing method.

BACKGROUND DISCUSSION

There is a technology for assisting diagnosis of a brain dysfunction such as dementia. For example, Japanese Patent Application Publication No. 2020-000483 A discloses a dementia diagnosis device that converts an uttered voice answered by a subject with respect to a predetermined question into text data, calculates an editing distance from text data for comparison, and determines whether or not there is a possibility that the subject has developed dementia.

Japanese Patent Application No. 2020-000483 A does not estimate a possibility of a brain dysfunction in consideration of a difference in symptoms of various brain dysfunctions such as dementia and aphasia.

SUMMARY

A program is disclosed that helps enable suitable estimation of the possibility of the brain dysfunction.

A non-transitory computer-readable medium storing computer program code executed by a computer processor is disclosed that executes a process comprising: outputting a first question by voice; receiving an answer to the first question from a subject; outputting a second question by text; receiving an answer to the second question from the subject; determining whether or not the answers to the first and second questions are correct; and estimating a possibility of a brain dysfunction of the subject based on correctness or incorrectness of the answers to the first and second questions.

An information processing device is disclosed, which includes: a processor configured to: output a first question by voice; receive an answer to the first question from a subject; output a second question by text; receive an answer to the second question from the subject; determine whether or not the answers to the first and second questions are correct; and estimate a possibility of a brain dysfunction of the subject based on correctness or incorrectness of the answers to the first and second questions.

An information processing method is disclosed, which includes: outputting, by a processor, a first question by voice; receiving, by the processor, an answer to the first question from a subject; outputting, by the processor, a second question by text; receiving, by the processor, an answer to the second question from the subject; determining, by the processor, whether or not the answers to the first and second questions are correct; and estimating, by the processor, a possibility of a brain dysfunction of the subject based on correctness or incorrectness of the answers to the first and second questions.

In one aspect, the possibility of the brain dysfunction can be suitably estimated.

BRIEF DESCRIPTION OF THE DRAWINGS

FIG. 9 is an explanatory view illustrating an example of a record layout of an answer history database (DB).

DETAILED DESCRIPTION

Set forth below with reference to the accompanying drawings is a detailed description of embodiments of a program, an information processing device, and an information processing method. Note that since embodiments described below are preferred specific examples of the present disclosure, although various technically preferable limitations are given, the scope of the present disclosure is not limited to the embodiments unless otherwise specified in the following descriptions.

First Embodiment

Figure 1:
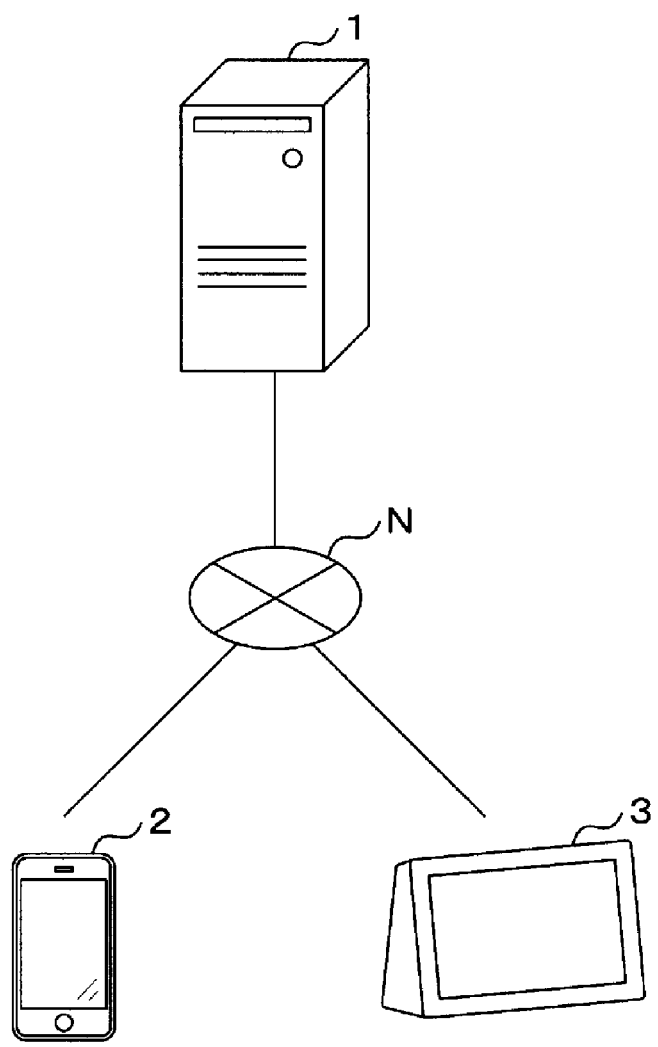
FIG. 1 is an explanatory view illustrating a configuration example of an interaction system.

FIG. 1 is an explanatory diagram illustrating a configuration example of an interaction system. In the present embodiment, the interaction system that determines the presence or absence of an abnormality, preferably a brain dysfunction, of a subject based on an uttered voice input by the subject will be described. The interaction system can include an information processing device 1, a mobile terminal 2, and a speaker terminal 3. The respective devices are connected for communication via a network N such as the Internet.

The information processing device 1 is an information processing device capable of various types of information processing and transmission and reception of information, and can be, for example, a server computer, a personal computer, or the like. In the present embodiment, the information processing device 1 is assumed to be a server computer, and is hereinafter rephrased as the server 1 for brevity. The server 1 can determine whether or not there is a possibility of a brain dysfunction from the uttered voice input by the subject. Specifically, as will be described later, the server 1 detects an abnormal point suspected of having a brain dysfunction from the uttered voice input by the subject as a message with respect to a chat group in which a plurality of users including the subject participate, an uttered voice input by the subject with respect to a chatbot system that operates based on a predetermined interaction engine (i.e., artificial intelligence chatbot), or the like.

A target brain dysfunction is not particularly limited, and examples of the target brain dysfunction can include dementia and aphasia. The server 1 detects abnormal utterances of the subject (ambiguous words, verbal errors, and the like) caused by dementia, aphasia, or the like, and presents an abnormal point to another user (for example, user related to the subject, such as a family member of the subject and a medical worker who treats the subject).

The mobile terminal 2 is an information processing terminal used by each of the users including the subject, and can be, for example, a smartphone, a tablet terminal, or the like. Only the single mobile terminal 2 is illustrated in FIG. 1, however, the mobile terminal 2 of each of the subject and the other users are connected to the server 1 (i.e., the interactive system can include two or more mobile terminals 2). The server 1 acquires, from the mobile terminal 2, the uttered voice input by the subject as the message or the like with respect to the chat group, and converts the uttered voice into a text. Then, the server 1 detects an abnormal point from the converted text.

The speaker terminal 3 is a voice input/output terminal installed in the home of the subject or the like, and can be, for example, a so-called smart speaker. The speaker terminal 3 is not limited to what is called a smart speaker as long as a voice input/output function and an image display function are provided. In addition, an installation place of the speaker terminal 3 is not limited to the home of the subject, and may be a facility other than the home (for example, a nursing care facility). The speaker terminal 3 can function as a terminal device of the chatbot system and interacts with the subject. The server 1 may acquire the uttered voice of the subject from the speaker terminal 3 to detect the abnormal point as will be described later.

The mobile terminal 2 and the speaker terminal 3 are exemplified as the terminal devices that cooperate with the server 1 in the present embodiment, but another form of terminal device (for example, a robot device) may be used. The terminal devices only need to be a local terminal having the voice input/output function, the image display function, and the like, and a form of the terminal devices are not particularly limited.

Figure 2:
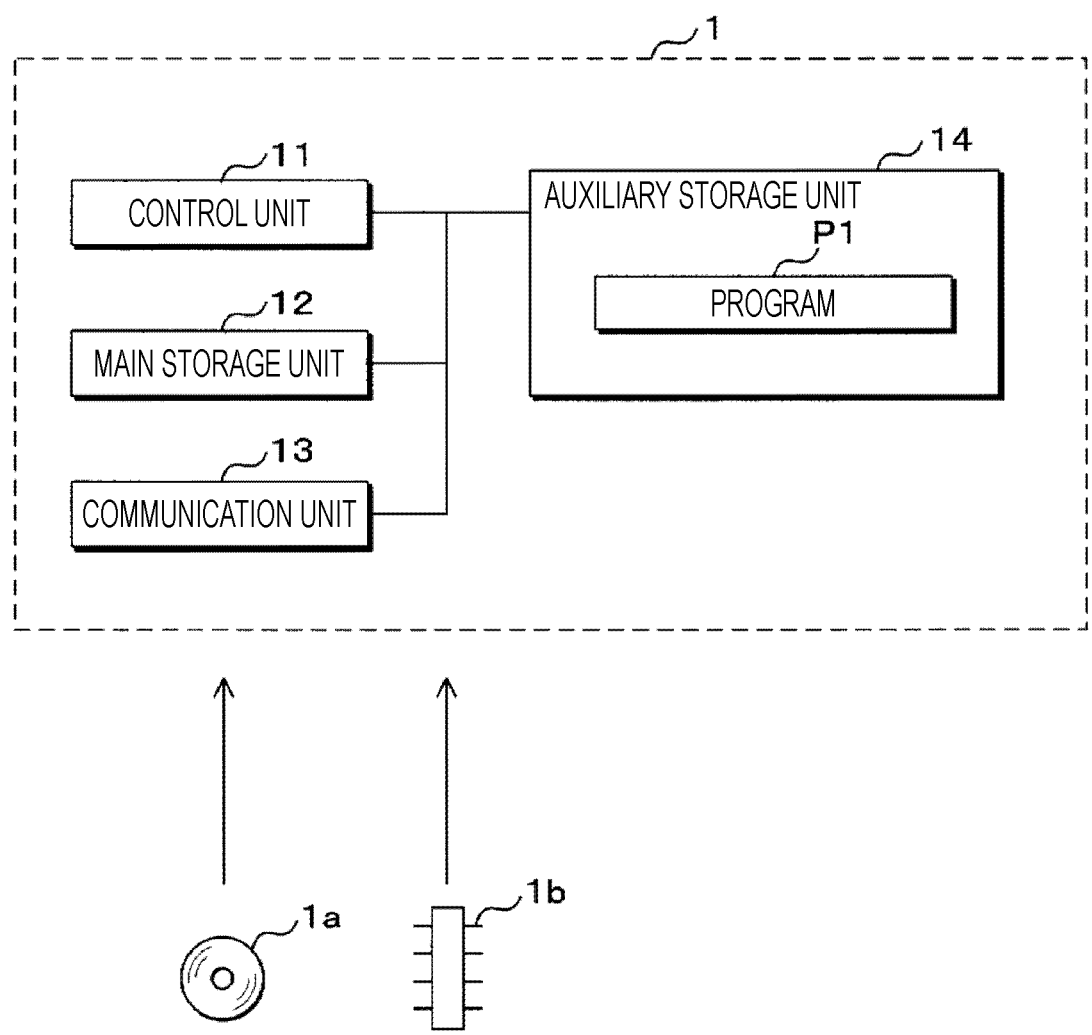
FIG. 2 is a block diagram illustrating a configuration example of a server.

FIG. 2 is a block diagram illustrating a configuration example of the server 1. The server 1 can include a control unit 11, a main storage unit 12, a communication unit 13, and an auxiliary storage unit 14.

The control unit 11 can include one or a plurality of arithmetic processing units such as a central processing unit (CPU), a micro-processing unit (MPU), and a graphics processing unit (GPU), and performs various types of information processing, control processing, and the like by reading and executing a program P1 stored in the auxiliary storage unit 14. The main storage unit 12 can be a temporary storage area such as a static random access memory (SRAM), a dynamic random access memory (DRAM), or a flash memory, and temporarily stores data necessary for the control unit 11 to execute arithmetic processing. The communication unit 13 is a communication module configured to perform processing related to communication, and transmits and receives information to and from the outside. The auxiliary storage unit 14 can be a non-volatile storage area such as a large-capacity memory or a hard disk, and stores the program P1 necessary for the control unit 11 to execute the processing and other data.

The auxiliary storage unit 14 may be an external storage device connected to the server 1. In addition, the server 1 may be a multi-computer including a plurality of computers, or may be a virtual machine virtually constructed by software.

In addition, the server 1 is not limited to the above configuration in the present embodiment, and may include, for example, an input unit that receives an operation input, a display unit that displays an image, and the like. In addition, the server 1 may include a reading unit that reads a portable storage medium 1a, such as a compact disk (CD)-ROM or a digital versatile disc (DVD)-ROM, and may read and execute the program P1 from the portable storage medium 1a. Alternatively, the server 1 may read the program P1 from a semiconductor memory 1b.

Figure 3:
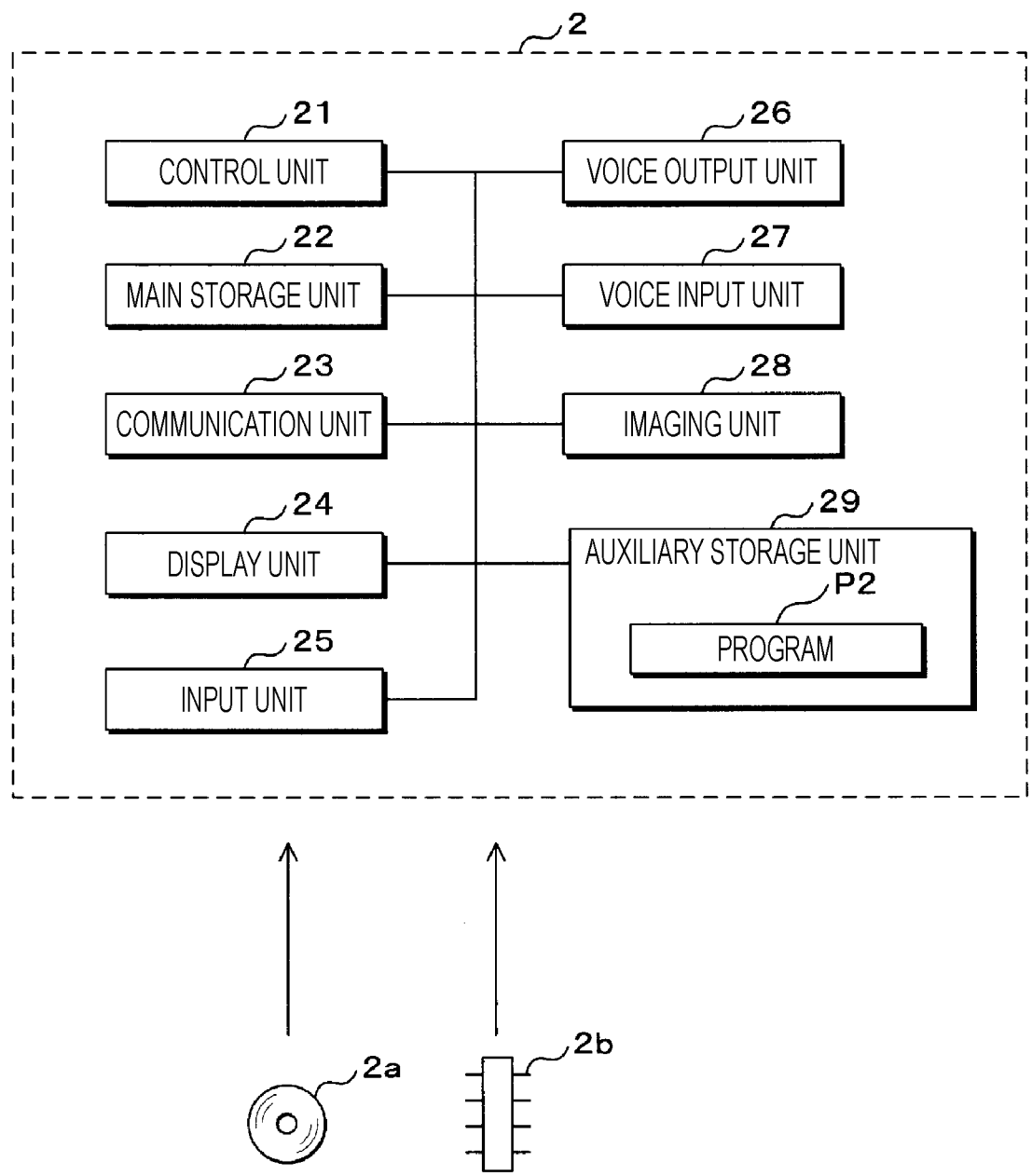
FIG. 3 is a block diagram illustrating a configuration example of a mobile terminal.

FIG. 3 is a block diagram illustrating a configuration example of the mobile terminal 2. The mobile terminal 2 can include a control unit 21, a main storage unit 22, a communication unit 23, a display unit 24, an input unit 25, a voice output unit 26, a voice input unit 27, an imaging unit 28, and an auxiliary storage unit 29.

The control unit 21 can include an arithmetic processing unit such as one or a plurality of CPUs and MPUs, and performs various types of information processing, control processing, and the like by reading and executing a program P2 stored in the auxiliary storage unit 29. The main storage unit 22 can be a temporary storage area such as a RAM, and temporarily stores data necessary for the control unit 21 to execute arithmetic processing. The communication unit 23 is a communication module configured to perform processing related to communication, and transmits and receives information to and from the outside. The display unit 24 is a display screen such as a liquid crystal display, and displays an image.

The input unit 25 is an operation interface such as a touch panel, and receives an operation input from a user. The voice output unit 26 is a speaker and outputs a voice. The voice input unit 27 is a microphone, and receives a voice input from the user. The imaging unit 28 is a camera including an imaging element such as a complementary MOS (CMOS), and captures an image. The auxiliary storage unit 29 is a non-volatile storage area such as a hard disk or a large-capacity memory, and stores the program P2 necessary for the control unit 21 to execute processing and other data.

The mobile terminal 2 may include a reading unit that reads a portable storage medium 2a such as a CD-ROM, and may read and execute the program P2 from the portable storage medium 2a. Alternatively, the mobile terminal 2 may read the program P2 from a semiconductor memory 2b.

Figure 4:
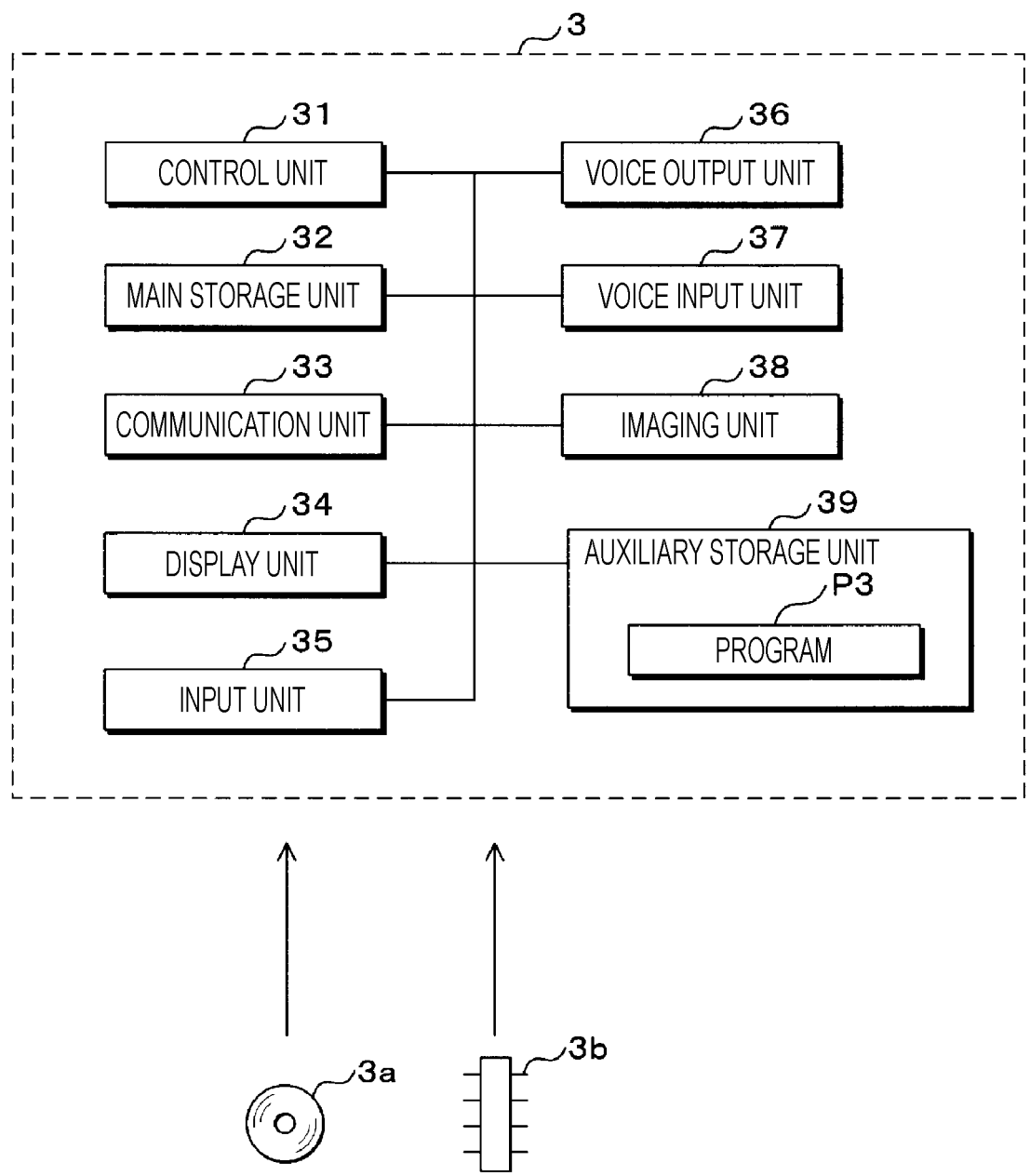
FIG. 4 is a block diagram illustrating a configuration example of a speaker terminal.

FIG. 4 is a block diagram illustrating a configuration example of the speaker terminal 3. The speaker terminal 3 includes a control unit 31, a main storage unit 32, a communication unit 33, a display unit 34, an input unit 35, a voice output unit 36, a voice input unit 37, an imaging unit 38, and an auxiliary storage unit 39.

The control unit 31 can include an arithmetic processing unit such as one or a plurality of CPUs and MPUs, and performs various types of information processing, control processing, and the like by reading and executing a program P3 stored in the auxiliary storage unit 39. The main storage unit 32 is a temporary storage area such as a RAM, and temporarily stores data necessary for the control unit 31 to execute arithmetic processing. The communication unit 33 is a communication module configured to perform processing related to communication, and transmits and receives information to and from the outside. The display unit 34 is a display screen such as a liquid crystal display, and displays an image.

The input unit 35 is an operation interface such as a touch panel, and receives an operation input from a user. The voice output unit 36 is a speaker and outputs a voice. The voice input unit 37 is a microphone, and receives a voice input from the user. The imaging unit 38 is a camera including an imaging element such as a CMOS, and captures an image. The auxiliary storage unit 39 is a non-volatile storage area such as a hard disk or a large-capacity memory, and stores the program P3 necessary for the control unit 31 to execute processing and other data.

The speaker terminal 3 may include a reading unit that reads the portable storage medium 3a such as a CD-ROM, and may read and execute the program P3 from the portable storage medium 3a. Alternatively, the speaker terminal 3 may read the program P3 from a semiconductor memory 3b.

Figure 5:
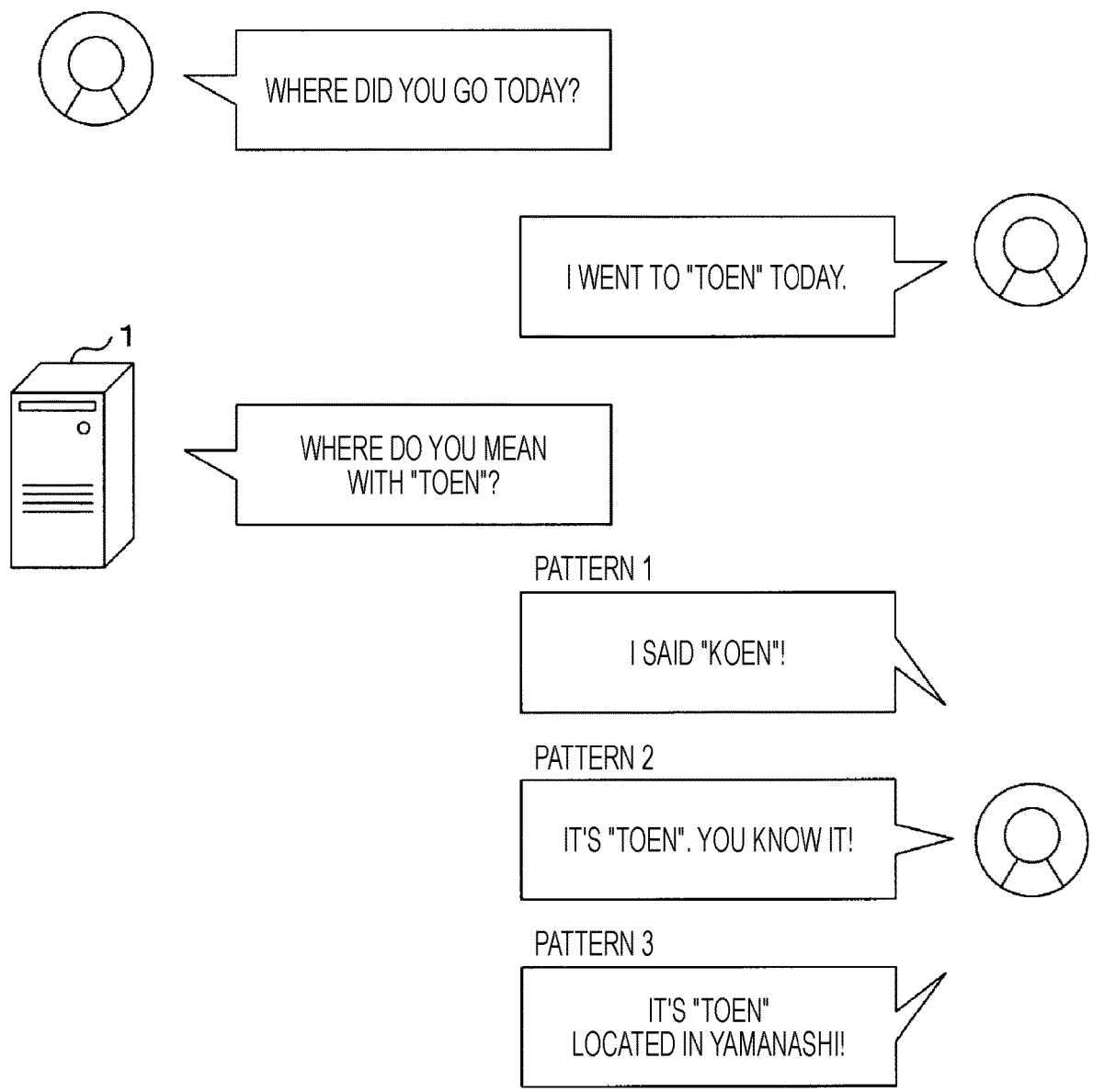
FIG. 5 is an explanatory view illustrating an outline of a first embodiment.

FIG. 5 is an explanatory view illustrating an outline of the first embodiment. The outline of the present embodiment will be described with reference to FIG. 5.

As described above, the server 1 determines whether or not a state of a subject is abnormal from messages or the like with respect to a chat group in which a plurality of users including the subject participate. FIG. 5 illustrates an interaction image in the chat group. The right side of FIG. 5 represents messages from the subject, and the left side represents messages from another user (for example, a family member) and a system (the server 1). The subject can also input a message by voice by inputting a text or utilizing a voice recognition function.

The server 1 converts the voice input by the subject into a text and detects an abnormal point from the converted text. The example of FIG. 5 illustrates a case where the server 1 has converted an uttered voice of the subject into a text "I went to "TOEN" today." in response to a message "Where did you go today?" from the other user. In this case, the server 1 detects an abnormal point "TOEN" from the text.

A specific method for detecting an abnormal point is not particularly limited, but for example, the server 1 performs morphological analysis to divide a text into a plurality of character strings (words), refers to a word dictionary (which is a database) storing a large number of words, and compares each of the character strings with each of the words in the word dictionary. The text is divided in the unit of a word in the present embodiment, but may be divided in a unit longer than the word (for example, a phrase), or may be divided in a unit shorter than the word. The server 1 detects a character string not stored in the word dictionary as an abnormal point. For example, the server 1 may define a word having a low appearance frequency (for example, word other than common words) in the word dictionary, and detect the word having the low appearance frequency as an abnormal point.

In addition, the server 1 may store a text related to a voice input by a subject and detect an abnormal point based on the past text. For example, the server 1 stores (registers) a character string obtained by dividing a text by morphological analysis in a word dictionary as a new word, and constructs a word dictionary for each subject.

Then, when a voice input from a subject is received and converted into a text, the server 1 detects an abnormal point by referring to the word dictionary corresponding to the subject. As a result, it is possible to improve the detection accuracy of the abnormal point in consideration of the tendency of the utterance of the subject.

An abnormal point can be detected using the word dictionary in the above description, the method for detecting an abnormal point is not limited to using a word dictionary. For example, the server 1 may also perform syntax analysis, semantic analysis, or the like of a text to detect an abnormal point. In addition, the detection method is not limited to a rule base, and for example, the server 1 may prepare a trained machine learning model (for example, a neural network) so as to detect an abnormal point when a text is input, and input a text obtained by converting an uttered voice into the model and detect an abnormal point. In this manner, the method for detecting an abnormal point is not particularly limited.

When detecting the abnormal point, the server 1 generates an interrogative sentence asking about the abnormal point and outputs the generated interrogative sentence to the mobile terminal 2 of the subject. The interrogative sentence is preferably in any format of 6W3H (Who, Whom, When, Where, What, Why, How, How many, and How Much). The server 1 applies a character string corresponding to the abnormal point to an interrogative sentence template in any format of 6W3H to generate the interrogative sentence. The server 1 outputs the interrogative sentence as a message in the chat group to be displayed on the mobile terminal 2. For example, the server 1 may convert the interrogative sentence into a voice and output the voice to the mobile terminal 2.

The server 1 receives an input of an answer in response to the interrogative sentence from the subject. The answer is input by voice in the same manner as when the message is input. The server 1 converts the input answer voice into a text, and determines whether or not a state of the subject is abnormal, specifically, for example, whether or not there is a possibility of a brain dysfunction.

FIG. 5 illustrates Patterns 1 to 3 as answer examples. In the case of Pattern 1, a correct word "KOEN (a park in Japanese)" is recognized from the voice, and thus, the server 1 determines that the state of the subject is normal. On the other hand, in the case of Pattern 2, an abnormal point "TOEN" is recognized again from the voice, and thus, the server 1 determines that the state of the subject is abnormal. In addition, in the case of Pattern 3, the character string "TOEN (a peach orchard)" is included, but a correct sentence is recognized from the voice in view of the preceding and subsequent contexts, and thus, the server 1 determines that the state of the subject is normal.

In this manner, the server 1 determines the state of the subject from the answer in response to the interrogative sentence. In this case, the server 1 may determine the state of the subject from data other than the voice. For example, the mobile terminal 2 captures an image of the subject at the time of inputting the answer in response to the interrogative sentence, and the server 1 determines the state of the subject from the captured image (for example, a moving image).

Specifically, the server 1 recognizes a face of the subject from the image, and determines the state of the subject from the bilateral asymmetry of the face. For example, in a case where a brain dysfunction occurs due to cerebral infarction, cerebral hemorrhage, or the like, asymmetric states and motions, such as different motions between the right and left sides of the face, lowering of one side, and distortion on one side, are observed on the right and left sides of the face. The server 1 divides a face area in the image into two right and left areas, identifies states (coordinates of feature points such as eyes and ends of a mouth) and motions (movements of the feature points) of the respective areas, and determines whether or not the right and left states and/or motions of the face are asymmetric. When it is determined to be asymmetric, the server 1 determines that the state of the subject is abnormal.

The image of the subject can be captured at the time of inputting the answer in response to the interrogative sentence in the above description, but an image of the subject may be captured at the time of inputting a voice of an initial message (message in which an abnormal point has been detected), and the bilateral asymmetry of the face may be determined from the image at the time of inputting the message (voice). That is, the time of capturing an image is not limited to the time of inputting an answer in response to an interrogative sentence, and may be the time of inputting a voice of a message.

In addition, the abnormality of the subject is determined by combining the image and the voice in the present embodiment, but the abnormality of the subject may be determined only from the voice (text).

As described above, the server 1 detects the abnormal point suspected of having the brain dysfunction from the text of the voice input by the subject as the message with respect to the chat group, asks about the abnormal point, and determines the state of the subject from the answer voice in response to the interrogative sentence and/or the image at the time of inputting the answer.

The case where the subject has a group chat with the other user has been described as an example in the above description, but the present embodiment is not limited where the subject has a group chat with the other user. For example, the server 1 may detect an abnormal point from an input voice when a subject interacts with a chatbot implemented based on a predetermined interaction engine.

The chatbot may perform input/output of a voice through the mobile terminal 2 such as a smartphone, or may perform input/output of a voice through the speaker terminal 3 (smart speaker) installed in the home of the subject or the like. Here, it is assumed that the speaker terminal 3 receives a voice input from the subject and outputs an answer voice.

The speaker terminal 3 receives various voice inputs, for example, daily greetings (such as "Good morning"), information output requests (for example, today's weather, schedule, and the like), and operation requests for devices (such as home electric appliances). The speaker terminal 3 performs various types of information processing in response to these input voices (for example, outputs a response voice for a greeting when the greeting is input, an answer voice of the greeting is output, outputs an operation signal for a device when a voice for operating the device is input, and the like). The server 1 acquires a voice input to the speaker terminal 3, converts the voice into a text, and detects an abnormal point. A method for detecting an abnormal point is similar to the above-described method.

In addition, the server 1 may call the subject from the system side via the speaker terminal 3 and receive a voice input. For example, the server 1 outputs a voice ("What is the weather today?" or the like) asking a predetermined matter to the speaker terminal 3 at a regular interval, and receives a voice input of an answer from the subject. As a result, for example, in a case where the subject is an elderly person living alone, it is possible to prompt the subject to have a regular conversation, and at the same time, it is possible to detect an abnormality of the subject from the conversation.

In this manner, the server 1 may detect the abnormal point from the uttered voice with the chatbot. That is, the voice from which an abnormal point is to be detected is not limited to the message to another user, and may be any uttered voice.

Figure 6:
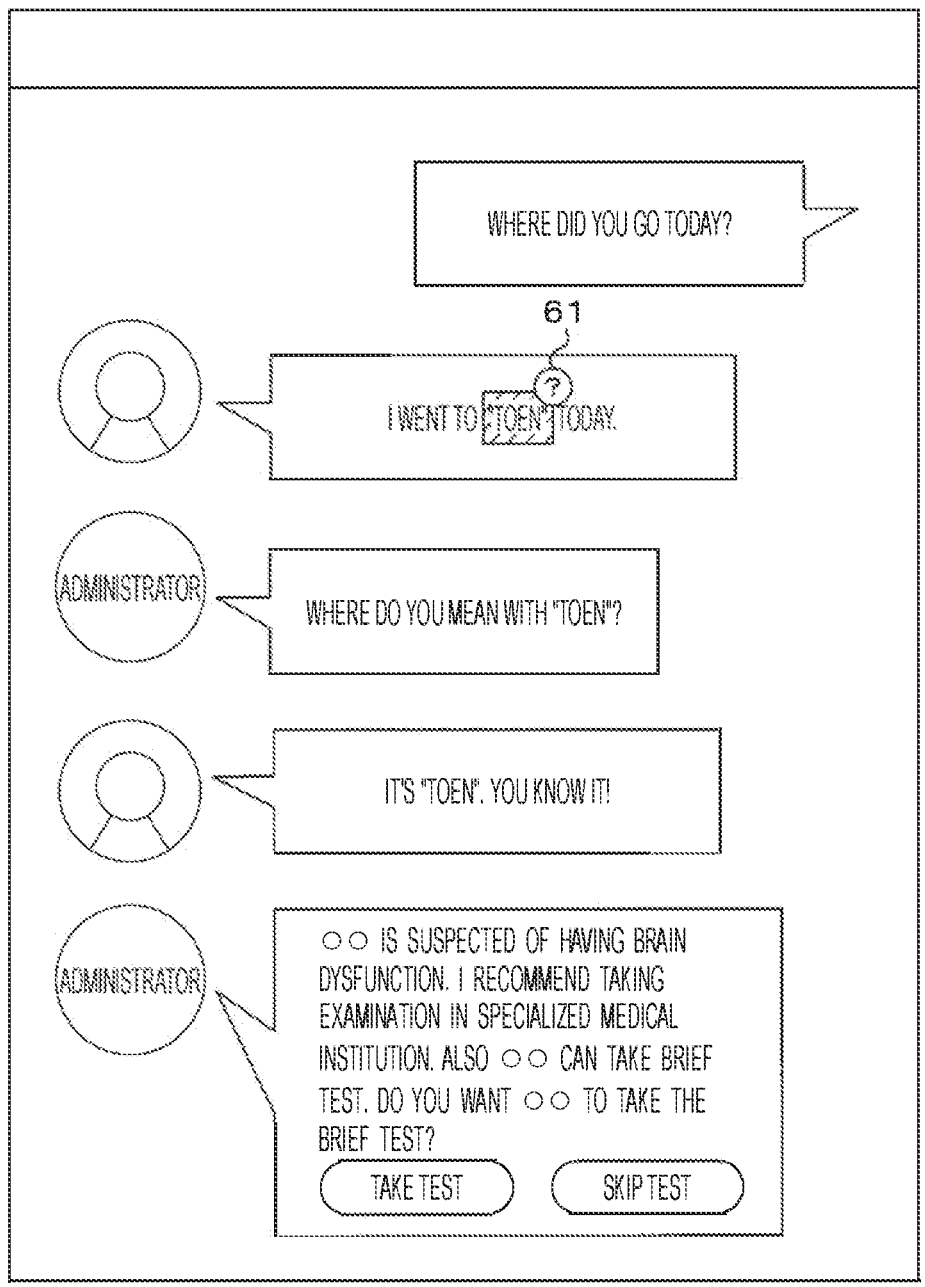
FIG. 6 is an explanatory view illustrating a display screen example of messages.

FIG. 6 is an explanatory view illustrating a display screen example of messages. FIG. 6 illustrates a state in which a message (text) in which an abnormal point has been detected is displayed in a group chat. Specifically, FIG. 6 illustrates a chat screen displayed by the mobile terminal 2 of another user (a family member or the like) who interchanges messages with a subject. FIG. 6 illustrates messages from the subject and the system on the left side, and messages from the other user on the right side.

When the abnormal point is detected from the message of the subject, the server 1 displays a character string corresponding to the abnormal point in a display mode different from those of the other character strings. For example, the server 1 changes a display color of the character string corresponding to the abnormal point and changes (highlights) a background color of the abnormal point. FIG. 6 illustrates a state in which the display color of the character string is changed in bold, and illustrates a state in which the background color is changed by hatching for convenience of the illustration. In addition, the server 1 displays an interrogative sentence output from the system side (server 1) and an answer of the subject in response to the interrogative sentence together.

In addition, the server 1 displays an object 61 corresponding to the abnormal point in the message of the subject. The object 61 may be an example of the display mode indicating the character string corresponding to the abnormal point, or may be an icon configured to reproduce a voice input by the subject. When an operation input to the object 61 is received, the server 1 outputs the input voice to the mobile terminal 2 and causes the mobile terminal 2 to reproduce the input voice. As a result, the other user (for example, a family member or the like) can listen to the input voice and confirm a state of the subject. The server 1 may be able to reproduce not only the initial voice from which the abnormal point has been detected but also a subsequent answer voice in response to the interrogative sentence.

Further, in a case where it is determined that the subject has the possibility of the brain dysfunction, the server 1 notifies the other user of the determination result.

For example, as illustrated in FIG. 6, the server 1 outputs a comment (information) indicating that there is the possibility of the brain dysfunction to the subject to be displayed on the mobile terminal 2. Specifically, the server 1 displays a comment for prompting the subject to take an examination in a medical institution and also prompting execution of a test for examining the presence or absence of a brain dysfunction. For example, the server 1 displays a button for selecting execution or non-execution of the test in the comment, and outputs test data to the mobile terminal 2 of the subject (or the mobile terminal 2 of the other user) when an operation input to a button "Take test" is received. The test data can be, for example, a calculation test such as addition and subtraction, a test for making a good guess with respect to an object shown in a photograph, or the like, but is not particularly limited.

The server 1 may notify not only the other user (for example, the family member or the like) related to the subject but also the subject himself/herself of the determination result indicating the possibility of the brain dysfunction.

As described above, it is possible to rather easily detect the abnormality of the subject and prompt the subject to take the medical examination or the like in the medical institution by detecting the abnormal point from the ordinary uttered voice (for example, the message to the chat group, the input voice to the chatbot, or the like) of the subject.

When a message in which an abnormal point has been detected is to be displayed, the server 1 may change a display mode of the abnormal point according to an answer in response to an interrogative sentence and/or a state of a subject determined from an image at the time of inputting the answer. For example, when the state of the subject has been determined to be abnormal from the answer voice in response to the interrogative sentence, the server 1 displays a character string corresponding to the abnormal point in red. On the other hand, when the abnormal point has been detected from the message, but the state of the subject has been determined to be normal from the answer voice in response to the interrogative sentence, the server 1 displays the character string corresponding to the abnormal point in blue. As a result, it is possible to present the abnormal point to the other user with a weight added to the degree of the abnormality, in a case, for example, where a simple verbal error is made or the like.

Figure 7:
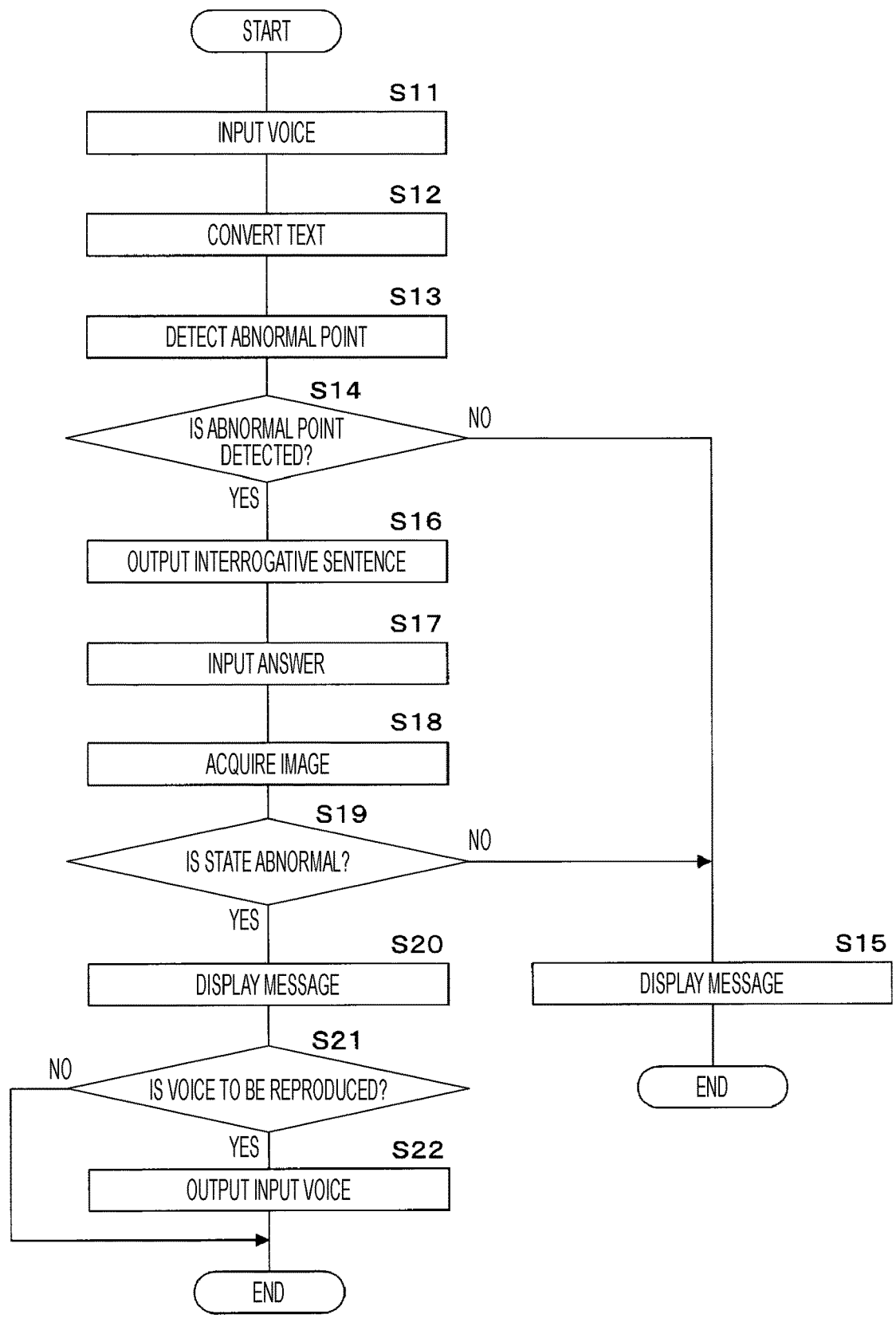
FIG. 7 is a flowchart illustrating a processing procedure executed by the server.

FIG. 7 is a flowchart illustrating a processing procedure executed by the server 1. A content of processing executed by the server 1 will be described with reference to FIG. 7.

The control unit 11 of the server 1 receives a voice input from a subject (S11). As described above, the voice can be, for example, a message to a chat group in which a plurality of users including the subject participate, but may be an input voice to a chatbot based on a predetermined interaction engine. The control unit 11 converts the input voice into a text (S12). The control unit 11 detects an abnormal point from the converted text (S13). For example, the control unit 11 performs morphological analysis of the text to divide the text into a plurality of character strings, compares each of the character strings with a word stored in a predetermined word dictionary, and detects a character string corresponding to an abnormal point.

The control unit 11 determines whether or not the abnormal point has been detected from the text (S14). When it is determined that no abnormal point has been detected (S14: NO), the control unit 11 outputs the converted text as a message of the subject to the mobile terminal 2 of another user to be displayed (S15). When it is determined that the abnormal point has been detected (S14: YES), the control unit 11 outputs an interrogative sentence asking back the character string corresponding to the abnormal point to the mobile terminal 2 of the subject (S16). The control unit 11 receives a voice input of an answer in response to the interrogative sentence from the subject (S17). In addition, the control unit 11 acquires an image obtained by capturing the subject at the time of inputting the answer from the mobile terminal 2 (S18).

The control unit 11 determines whether or not a state of the subject is abnormal based on the voice input in S17 and/or the image acquired in S18 (S19). Specifically, the control unit 11 determines whether or not there is a possibility of a brain dysfunction for the subject. For example, as in S14, the control unit 11 converts the input voice into a text, divides the text into a plurality of character strings, performs comparison with each of the words in the word dictionary, and determines whether or not there is a character string corresponding to the abnormal point. In addition, the control unit 11 recognizes a face of the subject from the image captured in S18, and determines whether or not right and left states and/or motions of the face are asymmetric. When it is determined that there is no abnormality (S19: NO), the control unit 11 shifts the processing to S15.

When determining that there is an abnormality (S19: YES), the control unit 11 causes the mobile terminal 2 of the other user to display a message (text) indicating the character string corresponding to the abnormal point in a display mode different from those of the other character strings (S20). Specifically, as described above, the control unit 11 changes a display color of the character string corresponding to the abnormal point and changes a background color of the character string for display. In addition, the control unit 11 displays the object 61 configured to reproduce the voice input by the subject.

The control unit 11 determines whether or not to reproduce the input voice according to an operation input to the object 61 (S21). When it is determined to reproduce the input voice (S21: YES), the control unit 11 causes the mobile terminal 2 of the other user to reproduce the voice input by the subject (S22). After executing the process of S22 or in the case of NO in S21, the control unit 11 ends the series of processing.

The server 1 executes processing such as the text conversion of the input voice and the detection of the abnormal point in the present embodiment for convenience of the description, but a part or all of the processing may be executed by the local mobile terminal 2 (or the speaker terminal 3) For example, the mobile terminal 2 may perform the text conversion, and the server 1 may perform the detection of the abnormal point. In this manner, a processing subject of the series of processing is not particularly limited.

As described above, according to the first embodiment, the voice input by the subject can be converted into the text to detect the abnormal point, and the character string corresponding to the abnormal point is displayed in the display mode different from those of the other character strings and is presented to the other user. As a result, the other user can rather easily grasp the abnormality of the subject.

In addition, according to the first embodiment, it is possible to detect the abnormality of the subject from the ordinary uttered voice of the subject such as the conversation message in the chat group and the input voice with respect to the chatbot.

In addition, according to the first embodiment, the detection accuracy of the abnormal point can be improved by referring to the text related to the past input voice of the subject.

In addition, according to the first embodiment, when the abnormal point is detected, it is possible to more suitably determine whether or not the state of the subject is abnormal by outputting the interrogative sentence asking back the abnormal point and receiving the input of the answer.

In addition, according to the first embodiment, it is possible to more suitably determine the abnormality of the subject related to the brain dysfunction by determining the bilateral asymmetry of the face from the image obtained by capturing the subject at the time of inputting the answer.

In addition, according to the first embodiment, the display mode of the character string corresponding to the abnormal point is changed according to the state of the subject determined from the answer in response to the interrogative sentence and/or the captured image of the subject, so that the abnormal point can be presented to the other user with the degree of abnormality added to weight.

In addition, according to the first embodiment, the other user can rather easily grasp the state of the subject since the voice input by the subject is reproduced.

Second Embodiment

In the first embodiment, the mode of detecting the abnormal point from the voice input by the subject has been described. In the present embodiment, a mode of estimating a possibility of a brain dysfunction by making a question by voice or text when an abnormal point is detected will be described. The same reference signs will be given to contents overlapping with those of the first embodiment, and the description of the same reference signs will be omitted.

Figure 8:
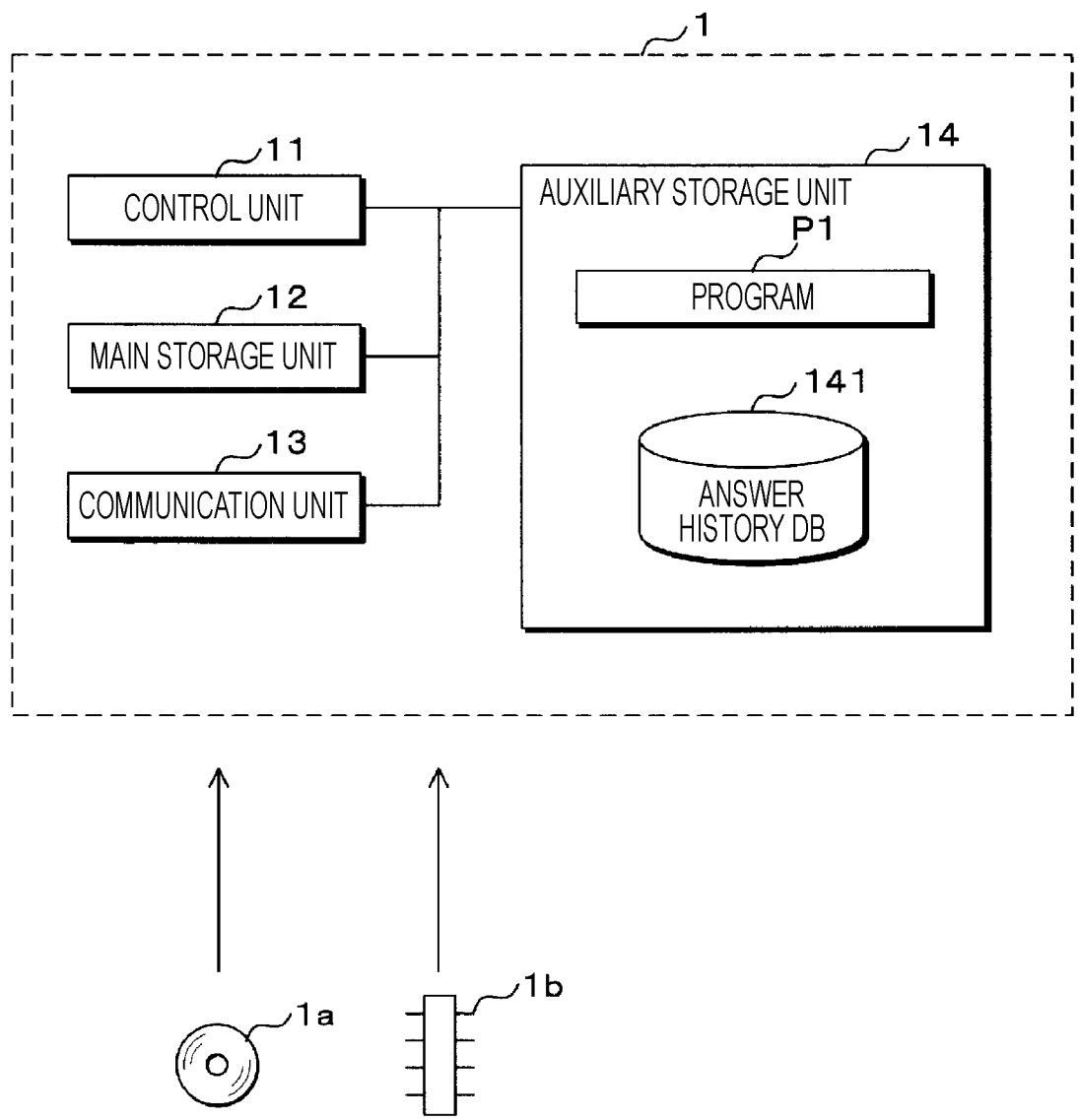
FIG. 8 is a block diagram illustrating a configuration example of a server according to a second embodiment.

FIG. 8 is a block diagram illustrating a configuration example of the server 1 according to a second embodiment. The auxiliary storage unit 14 of the server 1 according to the present embodiment stores an answer history database (DB) 141. The answer history DB 141 is a database that stores an answer of a subject in response to a question to be described later and an estimation result of the possibility of the brain dysfunction based on the answer.

FIG. 9 is an explanatory view illustrating an example of a record layout of the answer history DB 141. The answer history DB 141 can include a date and time column, a subject column, a voice column, a text column, a reaction column, an estimation result column, and an image column. The date and time column stores an answering date and time when the subject has answered a question. In association with the answering date and time, the subject column, the voice column, the text column, the reaction column, the estimation result column, and the image column can store a name of an answering subject, correctness or incorrectness of an answer to a voice question (first question to be described later), correctness or incorrectness of an answer to a text question (second question to be described later), a reaction of the subject to a question, an estimation result of the possibility of the brain dysfunction estimated based on an answer, and a captured image (for example, a moving image) obtained by capturing an image the subject at the time of answering, respectively. In the reaction column, not only determination results of the bilateral symmetry of a face, a motion of a finger or a line-of-sight direction, an expression, and the like determined from the captured image of the subject as will be described later but also an answering time from an output of a question to an input of an answer and the like can be stored.

Figure 10A:
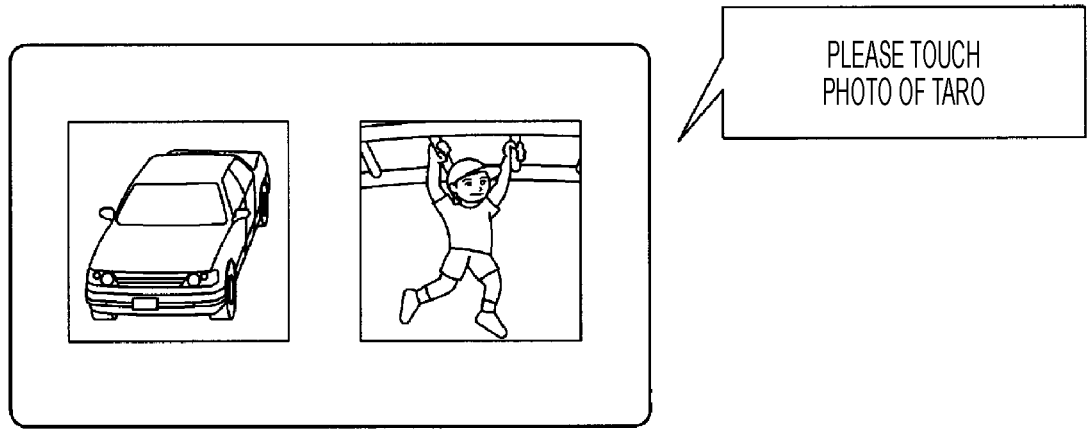
FIG. 10A is an explanatory view illustrating a display screen example of a speaker terminal.
Figure 10B:
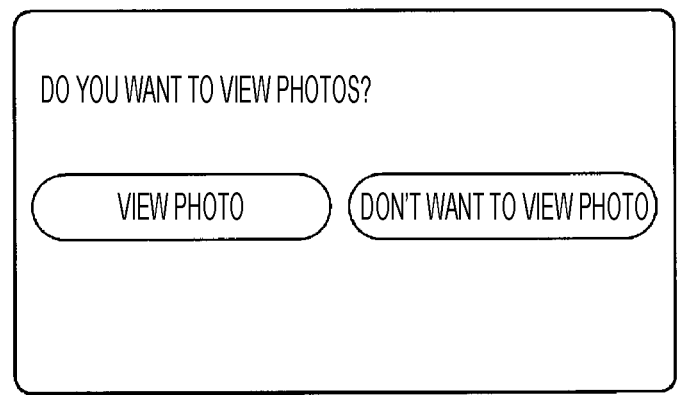
FIG. 10B is an explanatory view illustrating a display screen example of the speaker terminal.
Figure 11A:
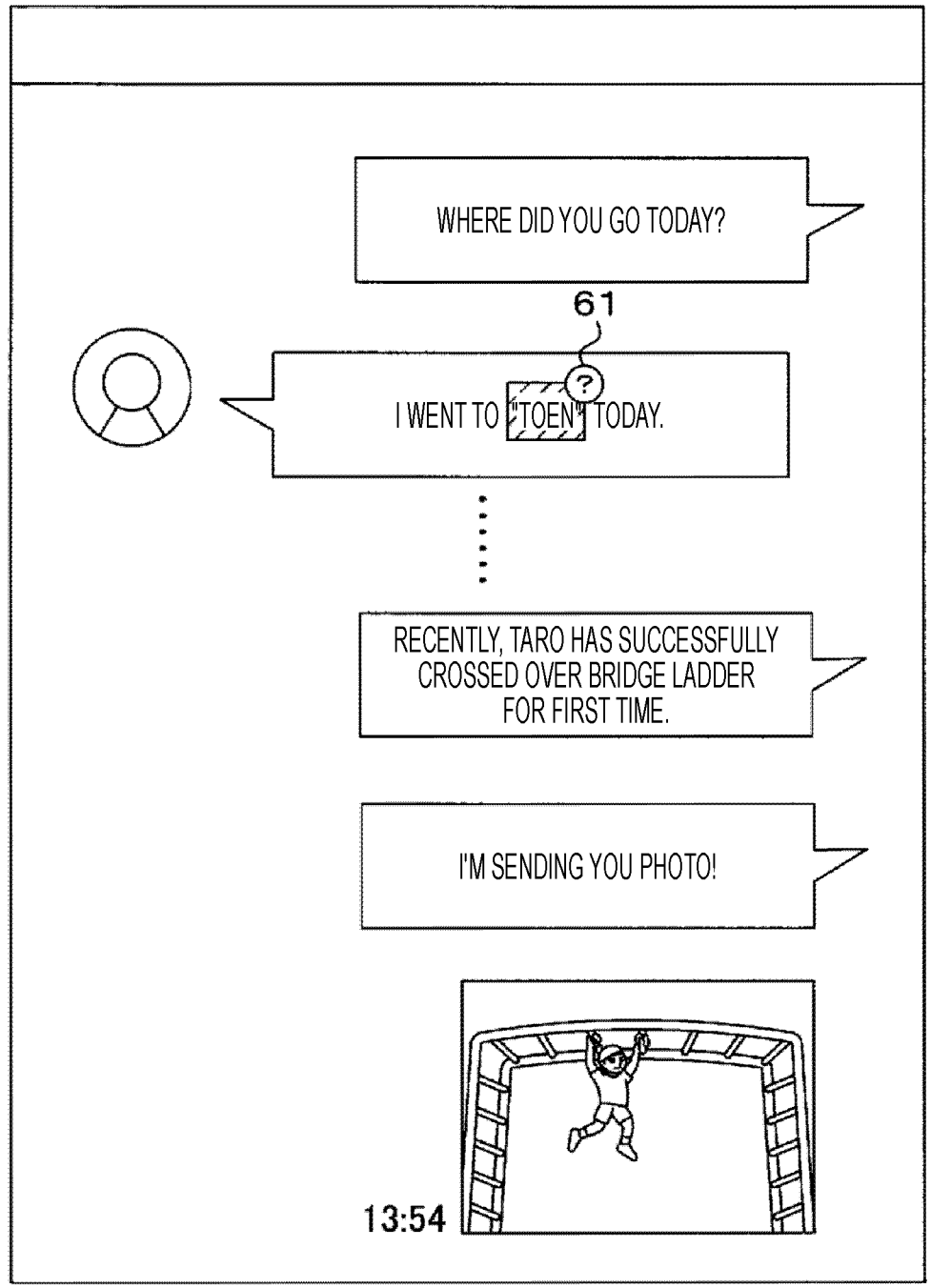
FIG. 11A is an explanatory view illustrating a display screen example of messages according to the second embodiment.
Figure 11B:
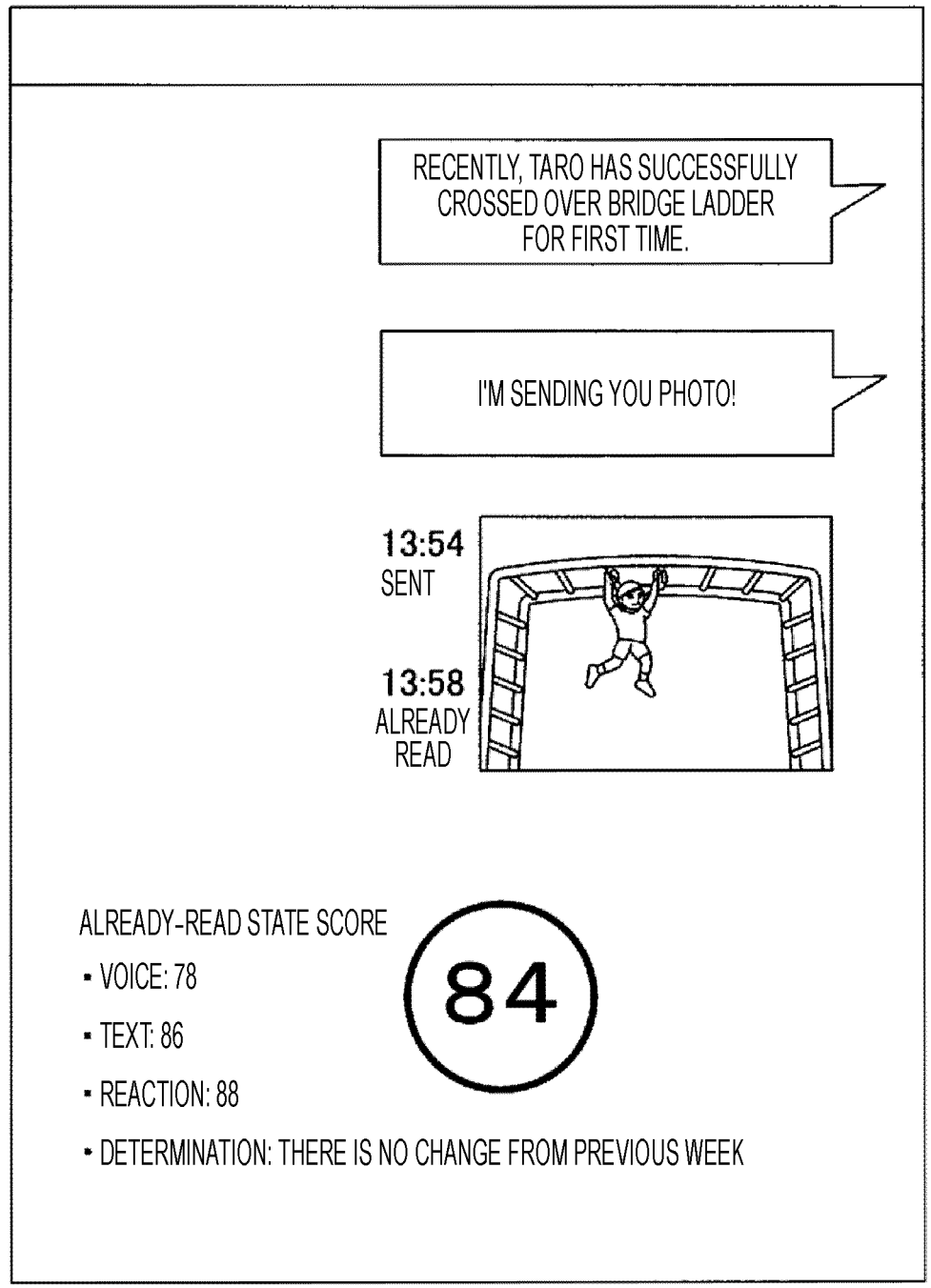
FIG. 11B is an explanatory view illustrating an example of a chat screen when an estimation result is displayed.

FIGS. 10A and 10B are explanatory views illustrating display screen examples of the speaker terminal 3. FIG. 11A is an explanatory view illustrating a display screen example of messages according to the second embodiment. FIG. 11B is an explanatory view illustrating an example of a chat screen when an estimation result is displayed. An outline of the present embodiment will be described with reference to FIGS. 10A, 10B, 11A, and 11B.

As described in the first embodiment, the server 1 detects an abnormal point from a voice input by the subject and presents the abnormal point to another user. In the present embodiment, the server 1 makes questions by voice and text to the subject when the abnormal point is detected. Then, the server 1 estimates a possibility of a brain dysfunction based on answers of the subject in response to the questions.

Specifically, the server 1 outputs a first question by voice and a second question by text to the speaker terminal 3, and causes the speaker terminal 3 to perform voice output and image display respectively corresponding to the questions. FIGS. 10A and 10B illustrate the screen example in a case where the first question is made and the screen example in a case where the second question is made, respectively. The server 1 causes the speaker terminal 3 to display answer options for each of the questions, and receives an input of an answer by receiving a screen operation for selecting one of the displayed options.

The question can be made via the speaker terminal 3 in the present embodiment, but the question may be made via the mobile terminal 2.

Before describing FIGS. 10A and 10B, a description will be given based on FIG. 11A. Similarly, FIG. 6, FIG. 11A illustrates a chat screen displayed by the mobile terminal 2 of the other user. When the abnormal point is detected from a text related to a voice input by the subject, the mobile terminal 2 displays a message of the subject in which the abnormal point has been detected as in the first embodiment.

In the present embodiment, the server 1 receives an input of a message with respect to the subject from the other user via the screen when the abnormal point is detected. A content of the message is not particularly limited, but it is preferable to receive an input of a message including an image. In the example of FIG. 11A, a message including an image, for example, of a relative (for example, a grandchild) of the subject is input as the message with respect to the subject.

The server 1 analyzes the message input from the other user and extracts data for generating the first and second questions. For example, the server 1 extracts a proper noun (for example, a name of a person, and the grandchild's name "Taro" in the examples of FIGS. 11A and 11B) in the text and the image. The server 1 generates the first and second questions based on the extracted data, and outputs the first and second questions to the speaker terminal 3.

The description will be continued returning to FIGS. 10A and 10B. First, the server 1 generates the first question by voice and outputs the first question to the speaker terminal 3. For example, as illustrated in FIG. 10A, the server 1 outputs the image extracted from the message of the other user and another image different from the image to the speaker terminal 3 to be displayed, and outputs a voice for prompting a screen operation for selecting one of the images.

For example, the server 1 extracts an image area in which a person (for example, a grandchild) appears from the image extracted from the message to generate a thumbnail image, and displays the thumbnail image on the speaker terminal 3. In addition, the server 1 displays an irrelevant image prepared in advance as another option. The number of displayed images is two in the example of FIG. 10A, but may be three or more. In addition, the image input by the other user is displayed in the present embodiment, but for example, an image may be prepared (registered) in a database in advance for each subject, and the image prepared in the database may be displayed.

The server 1 applies the proper noun (the name of the grandchild) extracted from the message in response to an interrogative sentence of a template, generates a voice prompting the selection of an image of a person corresponding to the proper noun, and outputs the voice to the speaker terminal 3.

The server 1 receives an input of an answer to the first question. Specifically, the server 1 receives a screen operation for selecting one of the plurality of images displayed on the speaker terminal 3. The input of the answer may be received by voice or the like.

When the input of the answer to the first question is received, the server 1 outputs the second question by text. For example, as illustrated in FIG. 10B, the server 1 displays an interrogative sentence asking whether or not to browse an image (for example, a photograph), and displays an object (for example, a button) for selecting whether or not to browse the image. FIG. 10B illustrates a case where a correct image (the image of the grandchild) is selected on the screen of FIG. 10A. In this case, "Do you want to view photos?" is displayed as the interrogative sentence. However, in a case where an incorrect image is selected on the screen of FIG. 10A, "Don't you want to view photos?" is displayed as the interrogative sentence.

The server 1 receives a screen operation for selecting one of two options of "View photo" and "Don't want to view photo". In a case where "View photo" is selected, the server 1 outputs the message of the other user to the speaker terminal 3. Specifically, the server 1 causes the speaker terminal 3 to display the image input by the other user. A text other than the image may also be displayed. In a case where "Don't want to view photo" is selected (or in a case where none of the buttons is operated), the server 1 waits for processing for a predetermined time, and ends the series of processing without displaying the message when the predetermined time has elapsed.

The server 1 determines whether or not the answers to the first and second questions are correct. Then, the server 1 estimates a possibility of a brain dysfunction based on correctness or incorrectness of the answers to the first and second questions. Specifically, the server 1 estimates whether or not there is a possibility of a brain dysfunction and estimates a type of possible brain dysfunction based on a combination of the correctness and incorrectness of the respective answers.

A brain dysfunction to be estimated is not particularly limited, for example, aphasia and dementia (or transient degradation in a cognitive function due to cerebral infarction or the like) can be estimated in the present embodiment. The server 1 estimates whether or not there is a possibility of aphasia and whether or not there is a possibility of dementia based on the combination of the correctness and incorrectness of the respective answers.

Specifically, the server 1 estimates that there is the possibility of aphasia in a case where the answer to the first question by voice is a wrong answer and the answer to the second question by text is a correct answer. In addition, the server 1 estimates that there is the possibility of dementia in a case where both of the answers to the first and second questions are wrong answers. In accordance with an embodiment, for example, the possibility of dementia can be estimated to be normal in a case where both the answers to the first and second questions are correct, and it is treated an accidental answering error in a case where only the answer to the second question is wrong.

Although aphasia and dementia are often confused, the aphasia is a disorder that affects language ability, and dementia is a disorder that affects general cognitive ability including non-language ability. Reactions to a voice and a text vary depending on which symptom it is. Therefore, the first question by voice and the second question by text are made to identify the aphasia and dementia based on a combination of correctness and incorrectness of the answers to the respective questions in the present embodiment.

In addition to the answers to the first and second questions, the server 1 estimates the possibility of the brain dysfunction based on an image of the subject captured at the time of answering. For example, the speaker terminal 3 can simultaneously capture an image of the subject when outputting the first question and/or the second question. The server 1 acquires the answers to the respective questions from the speaker terminal 3 and acquires the image at the time of answering to perform the estimation.

For example, the server 1 estimates the possibility of the brain dysfunction based on the bilateral asymmetry of the face of the subject as in the first embodiment. That is, the server 1 divides a face area in the image into two right and left areas, identifies states (for example, coordinates of feature points such as eyes and ends of a mouth) and motions (for example, movements of the feature points) of the respective areas, and determines whether or not the right and left states and/or motions of the face are asymmetric. As a result, the server 1 can detect a situation in which the brain dysfunction occurs due to cerebral infarction or the like.

In the present embodiment, the server 1 estimates the possibility of the brain dysfunction by determining, from the image, whether or not the subject is in a state of being distressed in answering in addition to the bilateral asymmetry of the face. Specifically, the server 1 detects, from the image, a specific event corresponding to the distress state as will be described below.

For example, the server 1 detects a hand (for example, finger) of the subject or a line-of-sight direction of the subject from the image, and determines whether or not a motion of the hand or the line-of-sight direction of the subject corresponds to a specific motion. Specifically, the subject is hesitating to select an option, the server 1 detects a motion in which the hand or the line-of-sight direction of the subject moves back and forth between the respective options (for example, images for the first question or buttons for the second question). For example, in the case of Broca's aphasia, when a verbal command is given to make a correct choice from a plurality of options, an event of showing distress in answering due to incomprehension of a content of the command and being indecisive over the options is observed. Therefore, the server 1 estimates the possibility of aphasia, for example, by detecting a hand or a line-of-sight direction from an image at the time of answering the first question by voice and determining whether or not the hand or the line-of-sight direction moves back and forth between the images.

In addition, for example, the server 1 may recognize an expression of the face of the subject and determine whether or not the expression corresponds to a specific expression (for example, being worried, anxious, embarrassed, or the like). In this case as well, it is possible to determine whether or not the subject is in the state of being distressed in answering similarly to the above.

In addition, for example, the server 1 may determine the distress state by estimating biological information of the subject from the image. The biological information can be, for example, an opening degree of a pupil, a pulse, a face temperature (body temperature), a blood flow rate, or the like. The server 1 can estimate the biological information from the image and can detect a change in the biological information (for example, the pupil is open, the pulse becomes fast, or the like) to determine whether or not the subject is in the state of being distressed in answering.

Although whether or not the subject is in the distressed state is determined from the image in the above description, for example, the server 1 may determine whether or not the subject is in the distressed state based on an answering time to a question in addition to the image. Specifically, the server 1 measures an answering time from an output of a question (for example, the first question) to an input of an answer, and determines whether or not the answering time is equal to or longer than a predetermined threshold. As a result, it is possible to detect a situation in which it takes time to answer the question because of being in the distress state.

As described above, the server 1 estimates the possibility of the brain dysfunction from the captured image of the subject and/or the answering time, in addition to the answers to the first and second questions. For example, even in a case where both the answers to the first and second questions are correct and the subject is estimated to be normal, the server 1 estimates that there is a possibility of a brain dysfunction in a case where the right and left motions and/or states of the face are asymmetric or in a case where it is determined that the subject is in the distress state. Alternatively, even in a case where the answer to the first question is correct and the answer to the second question is wrong so that it is treated as the accidental answering error of the subject, a process of repeating questions by changing interrogative sentences or the like may be performed in a case where the right and left motions and/or states of the face are asymmetric or in a case where it is determined that the subject is in the distress state.

The server 1 outputs an estimation result to the mobile terminal 2 of the other user to be displayed. FIG. 11B illustrates a chat screen when the estimation result is displayed. For example, the server 1 displays a text indicating the estimation result (determination result) and displays scores obtained by quantifying the estimation result.

The server 1 calculates scores of "Voice" corresponding to the first question, "Text" corresponding to the second question, and "Reaction" corresponding to the image and the answering time, and displays the scores on the mobile terminal 2. A method for calculating a score is not particularly limited, but for example, the server 1 counts correct/incorrect answers to the first and second questions made in a past predetermined period (for example, one week), calculates scores (for example, correct answer rates in the predetermined period) obtained by evaluating voice recognition ability and character recognition ability, respectively, and outputs the correct answer rates as the scores of "Voice" and "Text". In addition, for example, the server 1 calculates a degree of the distress state from the image and/or the answering time, and outputs the degree as the score of "Reaction".

Figure 12:
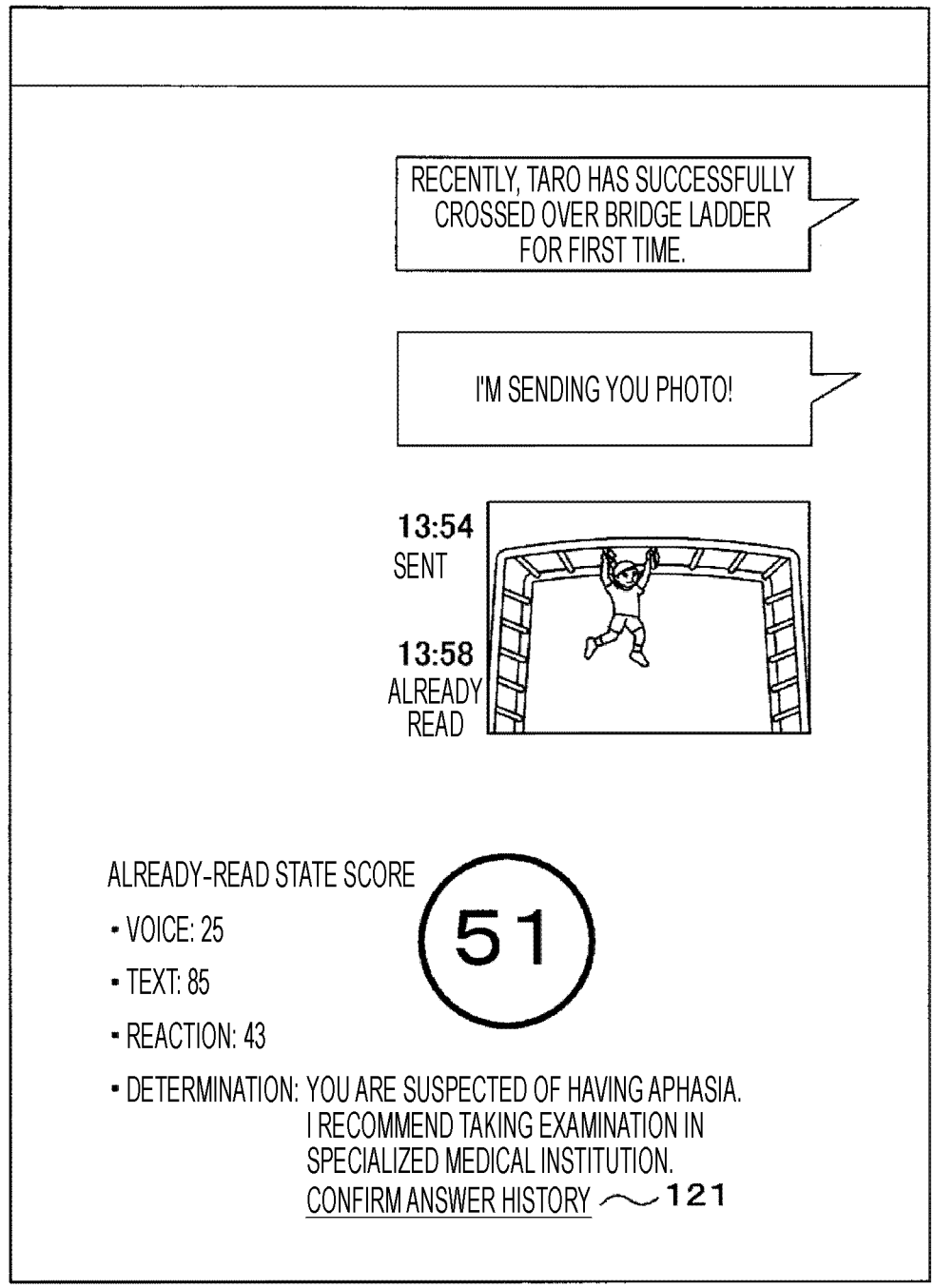
FIG. 12 is an explanatory view illustrating another example of a chat screen when an estimation result is displayed.

FIG. 12 is an explanatory view illustrating another example of the chat screen when the estimation result is displayed. FIG. 12 illustrates the chat screen in a case where it is estimated that there is a high possibility of the brain dysfunction. In a case where it is estimated that the possibility of the brain dysfunction is relatively high, the server 1 notifies the mobile terminal 2 of the other user of the estimation result to be displayed on the chat screen.

Specifically, the server 1 can display scores obtained by quantifying the estimation result as in FIG. 11B, and can display a text indicating that the possibility of the brain dysfunction is relatively high. For example, as illustrated in FIG. 12, the server 1 indicates a type of the brain dysfunction estimated to have a relatively high possibility, and displays a comment prompting the subject to take an examination in a medical institution.

The server 1 may notify not only the other user (for example, a family member or the like) related to the subject but also the subject himself/herself of the estimation result indicating the possibility of the brain dysfunction.

The server 1 further displays a link 121 for browsing (confirming) an answer history of the subject on the chat screen. The link 121 can be an object configured to output (display) history information indicating the history of past answers of the subject to the first and second questions and estimation results for the possibility of the brain dysfunction, and can be an object configured to transition to a history screen of FIG. 13. When an operation input with respect to the link 121 is received, the mobile terminal 2 transitions to the history screen in FIG. 13.

The history information may be made browsable even in a case where the state of the subject is estimated to be normal (FIG. 11B). In addition, it is a matter of course that the history information can be browsed at any time in addition to the transition from the chat screen.

Figure 13:
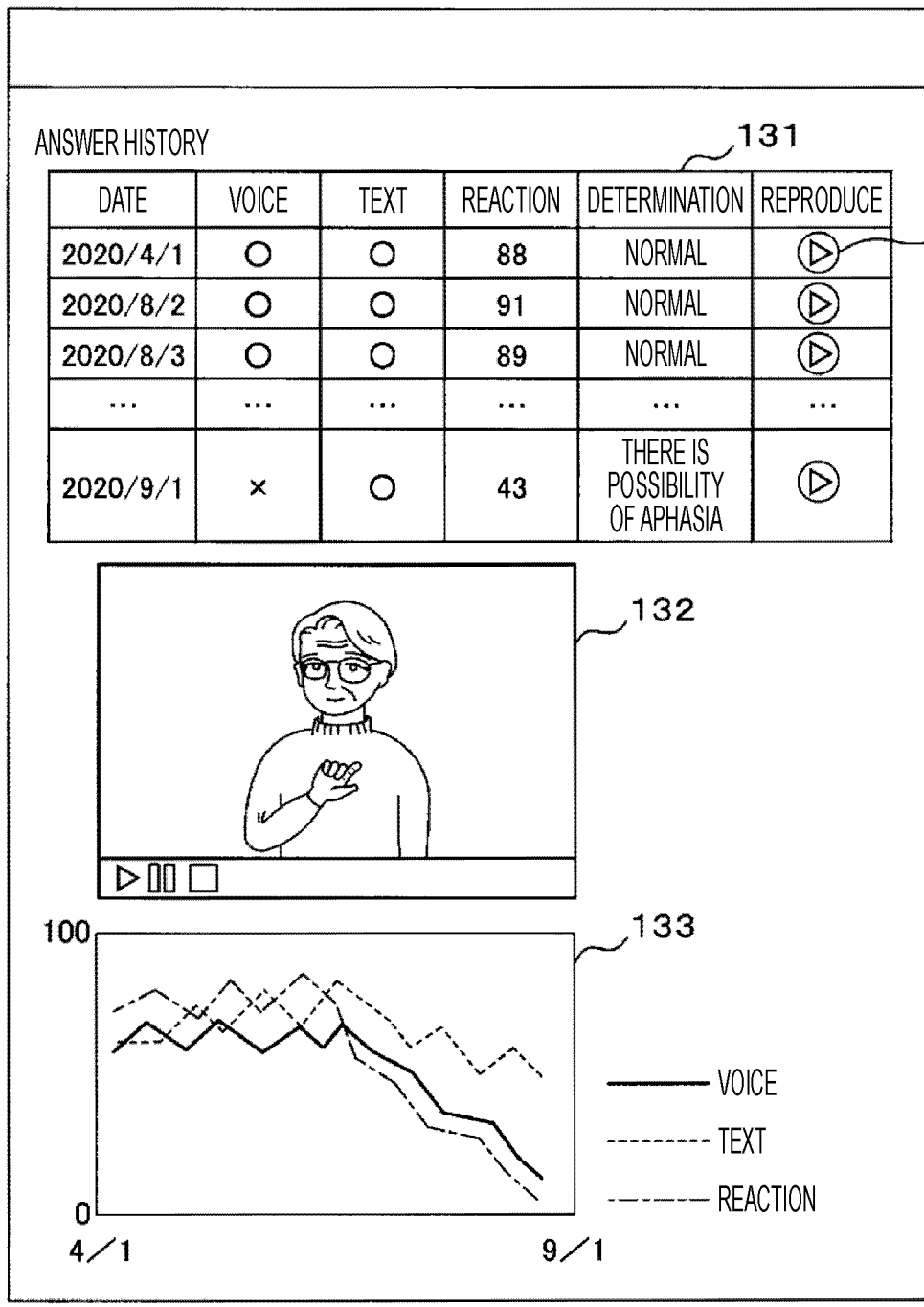
FIG. 13 is an explanatory view illustrating an example of a history screen.

FIG. 13 is an explanatory view illustrating an example of the history screen. The history screen is a display screen that displays a series of history information such as correctness or incorrectness of answers of the subject to the first and second questions, a captured image of the subject captured at the time of answering, and an estimation result of a brain dysfunction based on the answers and the image. The server 1 can store various types of history information in the answer history database (DB) 141, and outputs the history information in response to a request from the mobile terminal 2. For example, the history screen can include an answer history table 131, an image display field 132, and a score graph 133.

The answer history table 131 is a table showing a list of correctness or incorrectness of answers to the first and second questions ("Voice" and "Text") at each time point in the past, the degree of the distress state of the subject determined based on a captured image and the like at the time of answering (scores of "Reaction"), and the estimation result of the brain dysfunction ("Determination"). In addition, in the answer history table 131, a reproduction button 1311 for reproducing a captured image (moving image) is displayed in association with each time point.

The image display field 132 is a display field that displays images obtained by capturing the subject at the time of answering the first and/or second questions. In a case where an operation input with respect to the reproduction button 1311 is received, the mobile terminal 2 displays an image (moving image) captured at a corresponding time point.

The score graph 133 is a graph showing each of the scores illustrated in FIGS. 11B and 12 in time series. The mobile terminal 2 displays graphs (for example, line graphs) respectively indicating the scores of "Voice" obtained by evaluating the voice recognition ability based on correctness or incorrectness of answers to the first question, "Text" obtained by evaluating the character recognition ability based on correctness or incorrectness of answers to the second question, and "Reaction" obtained by evaluating states of the subject based on captured images or the like, and presents a change in the subject to the user.

As described above, in a case where an abnormal point is detected from an uttered voice of the subject, the server 1 outputs the first and second questions, and estimates the possibility of the brain dysfunction from correctness or incorrectness of answers to the respective questions, an image at the time of answering, and the like. As a result, an abnormality of the subject can be detected at a relatively early stage, and the brain dysfunction can be analyzed.

Figure 14:
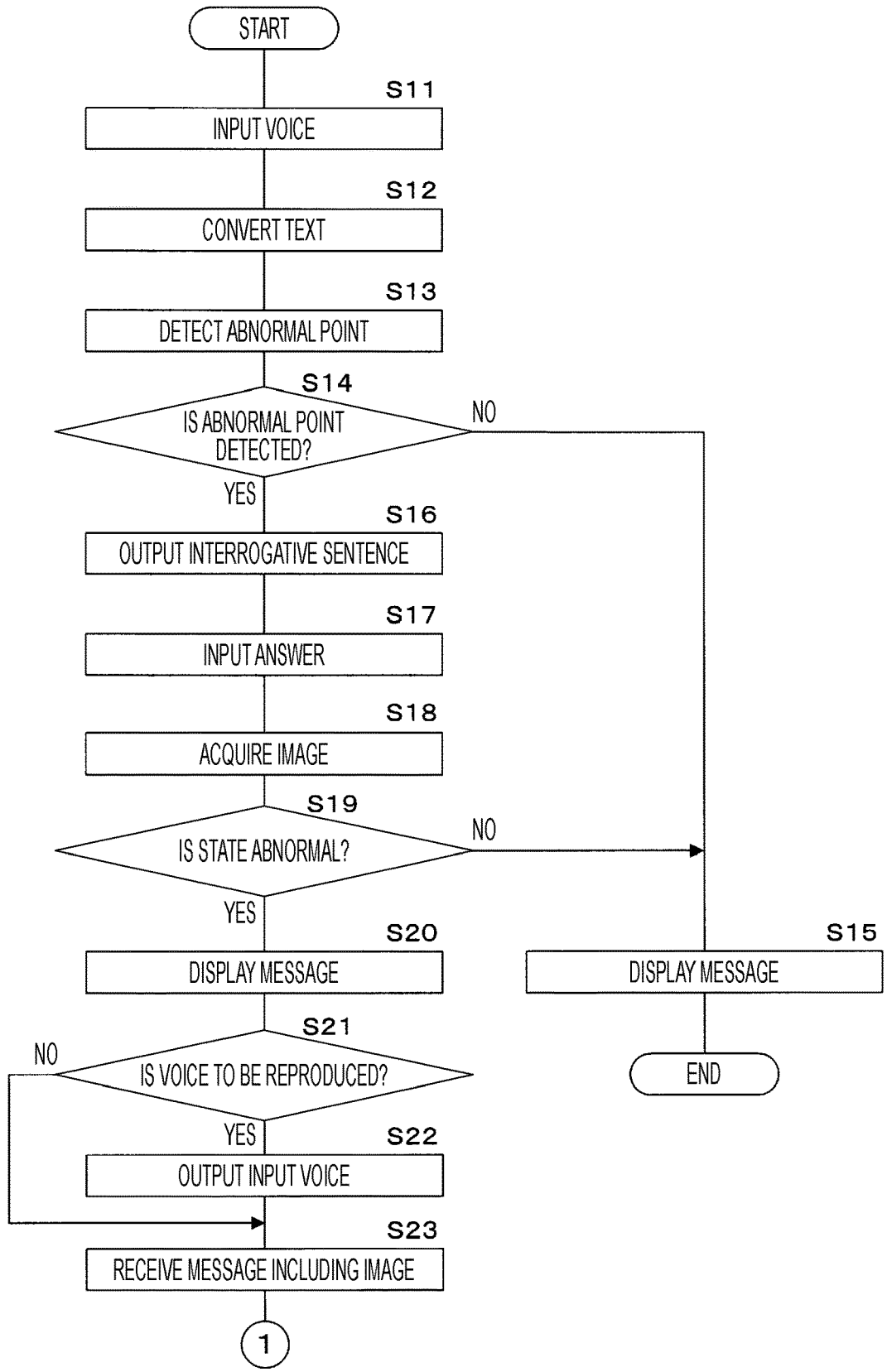
FIG. 14 is a flowchart illustrating an example of a processing procedure executed by the server according to the second embodiment.
Figure 15:
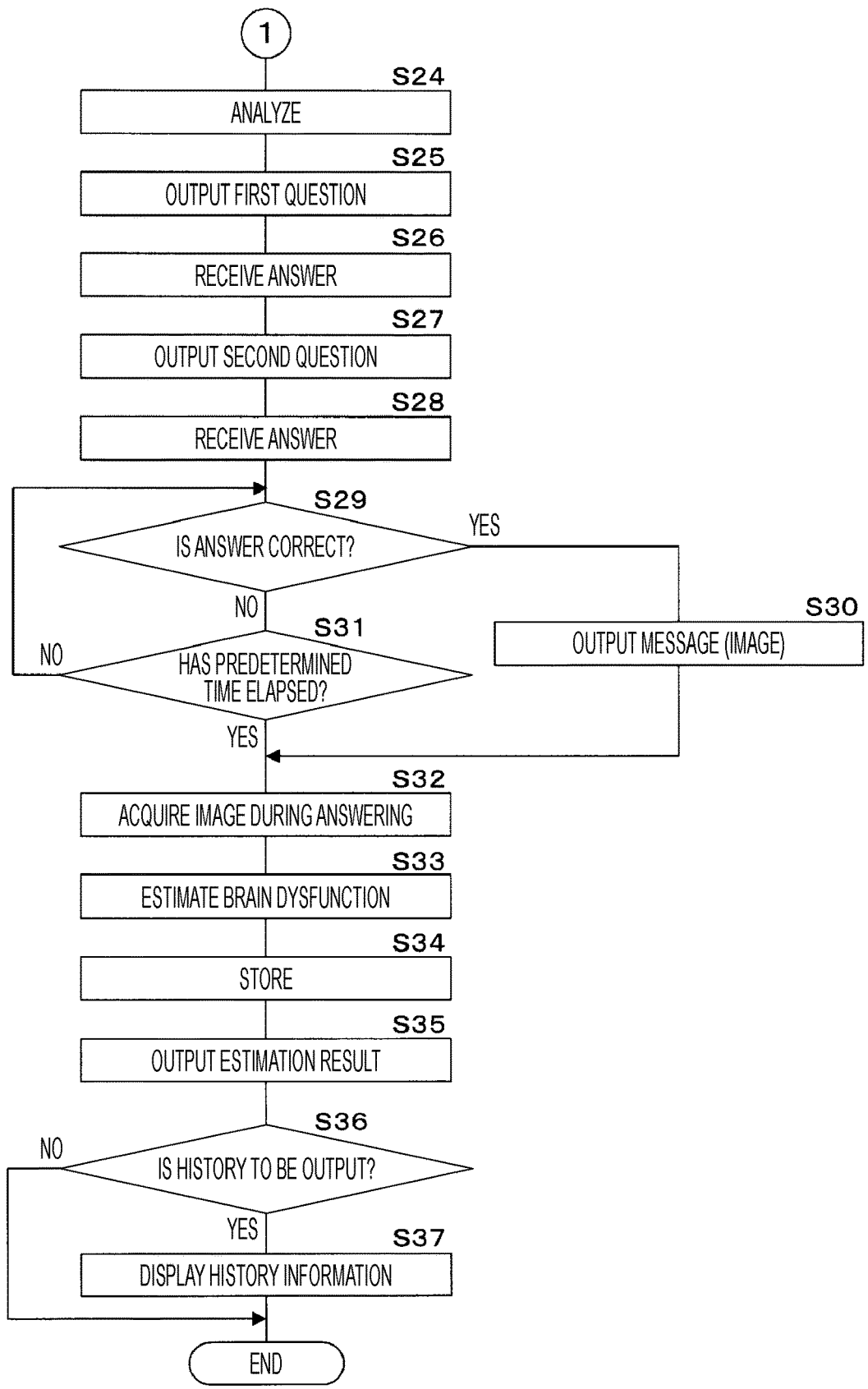
FIG. 15 is a flowchart illustrating an example of the processing procedure executed by the server according to the second embodiment.

FIGS. 14 and 15 are flowcharts illustrating an example of a processing procedure executed by the server 1 according to the second embodiment. After executing the process of S22 or in the case of NO in S21, the server 1 executes the following processes.

The control unit 11 of the server 1 receives an input of a message including an image from another user (S23). The control unit 11 analyzes the message, extracts the image included in the message, and extracts a proper noun or the like in a text (S24).

The control unit 11 outputs the first question by voice to the speaker terminal 3 based on the message analyzed in S24 (S25). For example, the control unit 11 causes the speaker terminal 3 to display, as options, a thumbnail image obtained by extracting a part of the image and another image different from the image, and outputs a voice prompting a screen operation for selecting one of the images. The control unit 11 receives an input of an answer to the first question (S26). Specifically, the control unit 11 receives an operation input for selecting one of the plurality of displayed images (options) as described above.

The control unit 11 outputs the second question by text to the speaker terminal 3 (S27). For example, the control unit 11 causes buttons for selecting whether or not to browse an image to be displayed as options, and causes the speaker terminal 3 to display a text asking whether or not to browse the image selected in S26. The control unit 11 receives an input of an answer to the second question (S28). For example, the control unit 11 receives an operation input for selecting one of the plurality of displayed buttons (options).

The control unit 11 determines whether or not the answer to the second question is correct (S29). For example, the control unit 11 determines whether or not a selection input for browsing the image has been received. If it is determined that the answer is correct (S29: YES), the control unit 11 outputs a message (image) from the other user to the speaker terminal 3 (S30).

If it is determined that the answer is not correct (S29: NO), the control unit 11 determines whether or not a predetermined time has elapsed since the output of the second question (S31). When it is determined that the predetermined time has not elapsed (S31: NO), the control unit 11 returns the processing to S29. After executing the process of S30 or in the case of YES in S31, the control unit 11 acquires an image obtained by capturing the subject at the time of answering in S26 and/or S28 from the speaker terminal 3 (S32).

The control unit 11 estimates a possibility of a brain dysfunction of the subject based on the answers to the first and second questions and the image of the subject at the time of answering and/or an answering time (S33). Specifically, the control unit 11 estimates whether or not there is the possibility of the brain dysfunction, and estimates a type of the brain dysfunction (aphasia and dementia). For example, in a case where the answer to the first question is wrong and the answer to the second question is correct, the control unit 11 estimates there is the possibility of aphasia is relatively high.

In addition, in a case where both the answers to the first and second questions are wrong, the control unit 11 estimates that the possibility of dementia is relatively high.

Further, the control unit 11 determines whether or not right and left states and/or motions of a face are asymmetric from the image of the subject at the time of answering. In addition, the control unit 11 determines whether or not the subject is in the distress state from the image of the subject and/or the answering time. Even in a case where it is estimated to be normal from the answers to the first and second questions, the control unit 11 estimates that there is a possibility of a brain dysfunction according to the bilateral asymmetry of the face and/or the determination result of the distress state. The control unit 11 stores, in the answer history DB 141, correctness or incorrectness of the answers to the first and second questions, the captured image of the subject at the time of answering, an estimation result of the possibility of the brain dysfunction, and the like (S34).

The control unit 11 outputs the estimation result to the mobile terminal 2 of the other user (S35). For example, the control unit 11 displays the estimation result as to whether or not there is a possibility of a brain dysfunction, calculates scores obtained by evaluating the subject based on the answer to the first question (voice), the answer to the second question (text), and the image of the subject at the time of answering and/or the answering time, and displays the scores on the mobile terminal 2.

The control unit 11 determines whether or not to output history information indicating a history of past answers of the subject to the first and second questions and estimation results of the possibility of the brain dysfunction based on the answers (S36).

For example, the control unit 11 determines whether or not an operation input with respect to the link 121 has been received on the chat screen illustrated in FIG. 12. When it is determined to output the history information (S36: YES), the control unit 11 outputs the history information to the mobile terminal 2 of the other user to be displayed (S37). Specifically, as described above, the control unit 11 displays the images obtained by capturing the subject and the like as the history information in addition to the answers to the first and second questions and the estimation results regarding the brain dysfunction at the respective time points in the past. After executing the process of S36 or in the case of NO in S36, the control unit 11 ends the series of processing.

The first and second questions are output when a message is input from another user in the above description, but the present embodiment is not limited thereto. For example, the server 1 may output the first and second questions to the speaker terminal 3 every certain period to receive inputs of answers regardless of the presence or absence of a message from another user. In this case, the server 1 may prepare an image for a question (the image of the grandchild in the above example) and the like in a database in advance, and generate the first and second questions using the image and the like. In this manner, the first and second questions may be output regardless of the presence or absence of a message from another user.

As described above, the possibility of the brain dysfunction can be suitably estimated by making the first question by voice and the second question by text according to the second embodiment.

In addition, it is possible to estimate the type of the brain dysfunction (preferably, aphasia and dementia) based on the combination of correctness and incorrectness of the answers to the respective questions according to the second embodiment.

In addition, it is possible to suitably prompt the input of the answer even in a case where the recognition ability has been degraded due to the brain dysfunction by displaying the answer options on the speaker terminal 3 and receiving the input of the answer by the screen operation according to the second embodiment.

In addition, the question is started when the abnormal point is detected from the uttered voice of the subject according to the second embodiment. As a result, it is possible to detect the brain dysfunction at a relatively early stage.

In addition, the first and second questions are generated from the message of the other user who is an interaction partner of the subject according to the second embodiment. As a result, it is possible to make a question in accordance with the subject.

In addition, the possibility of the brain dysfunction is estimated based on the image of the subject at the time of answering and/or the answering time as well as the answers according to the second embodiment. As a result, it is possible to detect a state in which cerebral infarction or the like has occurred (the bilateral asymmetry of the face) or a state of being distressed in answering, and it is possible to more suitably estimate the possibility of the brain dysfunction.

It is supposed that the embodiments disclosed herein are considered to be examples in all respects and not to be restrictive. The scope of the present disclosure is indicated not by the above meaning but by the claims and is intended to include all changes within the meaning and scope equivalent to the claims.

The detailed description above describes embodiments of a program, an information processing device, and an information processing method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A non-transitory computer-readable medium storing computer program code executed by a computer processor that executes a process comprising:
    acquiring a text obtained by converting a voice input from a subject;
    detecting abnormal utterances of the subject;
    outputting first and second questions when the abnormal utterances of the subject are detected, and wherein the detection of the abnormal utterances of the subject comprises detecting an abnormal point from the text;
    outputting the first question by voice;
    receiving an answer to the first question from the subject;
    outputting second question by text;
    receiving an answer to the second question from the subject;
    inputting the answers to the first and second questions into a machine learning model;
    determining by the machine learning model whether or not the answers to the first and second questions are correct;
    estimating a possibility of a brain dysfunction of the subject based on correctness or incorrectness of the answers to the first and second questions;
    estimating the possibility of the brain dysfunction and a type of the brain dysfunction based on a combination of correctness and incorrectness of the answers to the first and second questions;
    estimating that there is a possibility of aphasia in a case where the answer to the first question is wrong and the answer to the second question is correct and that there is a possibility of dementia in a case where both the answers to the first and second questions are wrong; and
    notifying the subject or another user related to the subject of an estimation result of the possibility of the brain dysfunction and that the subject should be examined in a medical institution to confirm that there is the possibility of aphasia in the case where the answer to the first question is wrong and the answer to the second question is correct and that there is the possibility of dementia in the case where both the answers to the first and second questions are wrong.

2. The computer-readable medium according to claim 1, further comprising:
    displaying options for the answers to the first and second questions on a display unit; and
    receiving a screen operation for selecting one of the displayed options to receive inputs of the answers to the first and second questions.

3. The computer-readable medium according to claim 1, further comprising:
    receiving a voice input from the subject of a message with respect to a chat group in which a plurality of users including the subject participate;
    converting the message is converted into the text to detect the abnormal point; and
    displaying the text indicating a character string corresponding to the abnormal point in a display mode different from display modes of other character strings on a terminal device of another user when the abnormal point is detected.

4. The computer-readable medium according to claim 3, further comprising:
    receiving an input of a message from the terminal device of the another user on which the text has been displayed;
    generating the first and second questions based on the message of the another user; and
    outputting the generated first and second questions.

5. The computer-readable medium according to claim 1, further comprising:
    acquiring an image obtained by capturing the subject when answering the first or second question; and
    estimating the possibility of the brain dysfunction based on correctness or incorrectness of the answers to the first and second questions and the image.

6. The computer-readable medium according to claim 5, further comprising:
    determining whether or not right and left motions or states of a face of the subject are asymmetric based on the image; and
    estimating that there is the possibility of the brain dysfunction in a case where it is determined that there is asymmetry.

7. The computer-readable medium according to claim 5, further comprising:
    determining whether or not the subject is in a state of being distressed in answering based on the image; and
    estimating that there is the possibility of the brain dysfunction in a case where it is determined that the subject is in the state of being distressed in answering.

8. The computer-readable medium according to claim 1, further comprising:
    measuring an answering time from an output of the first or second question to reception of an input of the answer; and
    estimating the possibility of the brain dysfunction based on correctness or incorrectness of the answers to the first and second questions and the answering time.

9. The computer-readable medium according to claim 1, further comprising:
    storing the answers to the first and second questions and an estimation result of the brain dysfunction based on correctness or incorrectness of the answers in a storage unit; and outputting history information indicating a history of the answers and the estimation result.

10. The computer-readable medium according to claim 1, further comprising:
outputting the first question and the second question by voice to the subject at predetermined intervals.

11. The computer-readable medium according to claim 1, further comprising:
outputting a predetermined matter by voice to the subject at regular intervals;
receiving a voice input of an answer to the predetermined matter from the subject; and
detecting an abnormality of the subject based on the answer to the predetermined matter.

12. The computer-readable medium according to claim 1, wherein the subject is a person that lives alone.

13. An information processing device comprising:
a processor configured to:
acquire a text obtained by converting a voice input from a subject;
detecting abnormal utterances of the subject;
detect an abnormal point from the text;
output first and second questions when the abnormal point is detected;
output the first question by voice;
receive an answer to the first question from the subject;
output the second question by text;
receive an answer to the second question from the subject;
input the answers to the first and second questions into a machine learning model;
determine by the machine learning model whether or not the answers to the first and second questions are correct;
estimate a possibility of a brain dysfunction of the subject based on correctness or incorrectness of the answers to the first and second questions estimate the possibility of the brain dysfunction and a type of the brain dysfunction based on a combination of correctness and incorrectness of the answers to the first and second questions;
estimate that there is a possibility of aphasia in a case where the answer to the first question is wrong and the answer to the second question is correct and that there is a possibility of dementia in a case where both the answers to the first and second questions are wrong; and
notify the subject or another user related to the subject of an estimation result of the possibility of the brain dysfunction and that the subject should be examined in a medical institution to confirm that there is the possibility of aphasia in the case where the answer to the first question is wrong and the answer to the second question is correct and that there is the possibility of dementia in the case where both the answers to the first and second questions are wrong.

14. The device according to claim 13, wherein the processor is further configured to:
output the first question and the second question by voice to the subject at predetermined intervals.

15. An information processing method comprising:
acquiring, by the processor, a text obtained by converting a voice input from a subject;
detecting, by the processor, an abnormal point from the text;
outputting, by the processor, first and second questions when the abnormal point is detected;
outputting, by a processor, the first question by voice;
receiving, by the processor, an answer to the first question from the subject;
outputting, by the processor, the second question by text;
receiving, by the processor, an answer to the second question from the subject;
inputting, by the processor, the answers to the first and second questions into a machine learning model;
receiving, by the processor, whether or not the answers to the first and second questions are correct from the machine learning model;
estimating, by the processor, a possibility of a brain dysfunction of the subject based on correctness or incorrectness of the answers to the first and second questions estimating, by the processor, the possibility of the brain dysfunction and a type of the brain dysfunction based on a combination of correctness and incorrectness of the answers to the first and second questions;
estimating, by the processor, that there is a possibility of aphasia in a case where the answer to the first question is wrong and the answer to the second question is correct and that there is a possibility of dementia in a case where both the answers to the first and second questions are wrong; and
notifying, by the processor, the subject or another user related to the subject of an estimation result of the possibility of the brain dysfunction and that the subject should be examined in a medical institution to confirm that there is the possibility of aphasia in the case where the answer to the first question is wrong and the answer to the second question is correct and that there is the possibility of dementia in the case where both the answers to the first and second questions are wrong.

16. The method according to claim 15, further comprising:
displaying, by the processor, options for the answers to the first and second questions on a display unit; and
receiving, by the processor, a selection of one of the displayed options to receive inputs of the answers to the first and second questions.

17. The method according to claim 15, further comprising:
outputting the first question and the second question by voice to the subject at predetermined intervals.

* * * * *